(12) United States Patent
Barmatov et al.

(10) Patent No.: US 11,814,570 B2
(45) Date of Patent: Nov. 14, 2023

(54) AMIDE EMULSIFIER FOR HIGH-TEMPERATURE OIL-BASED DRILLING FLUID

(71) Applicant: Schlumberger Technology Corporation, Sugar Land, TX (US)

(72) Inventors: Evgeny Borisovich Barmatov, Cambridge (GB); Dimitri M. Khramov, Katy, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 17/820,684

(22) Filed: Aug. 18, 2022

(65) Prior Publication Data

US 2023/0072831 A1 Mar. 9, 2023

Related U.S. Application Data

(60) Provisional application No. 63/260,398, filed on Aug. 19, 2021.

(51) Int. Cl.
*C09K 8/36* (2006.01)
*C07D 207/12* (2006.01)
*C07D 307/22* (2006.01)

(52) U.S. Cl.
CPC .............. *C09K 8/36* (2013.01); *C07D 207/12* (2013.01); *C07D 307/22* (2013.01)

(58) Field of Classification Search
None
See application file for complete search history.

(56) References Cited

U.S. PATENT DOCUMENTS 2,588,808 A    3/1952    Dawson
2,793,996 A    5/1957    Lummus
(Continued)

FOREIGN PATENT DOCUMENTS

EP    0403437 A2    12/1990
WO    8911516 A1    11/1989
(Continued)

OTHER PUBLICATIONS

Hilfiger et al., "Investigating the Chemical Nature of Flat Rheology", SPE-180320-MS, SPE Deepwater Drilling and Completions Conference, Sep. 14-15, 2016, 11 pages.
(Continued)

*Primary Examiner* — John J Figueroa

(57) ABSTRACT

Drilling fluid compositions include an emulsifier having a generic structure A, structure B, or a combination thereof. Structure A includes an amide (e.g., amic acid group) and structure B includes a cyclic imide. The emulsifier of the emulsifier system is formed by reacting a fatty oil amine (e.g., oleyl amine), with a cyclic anhydride (e.g., succinic anhydride) in the absence of diluent or in a diluent that does not react with the starting materials. The reaction takes place via application of a stepwise increase in temperature. An emulsifier based on structure A is formed when the reaction temperature is maintained at 50 to 100° C. for 1 to 3 hours. A further increase in reaction temperature (e.g., up to 200° C.) can include water elimination which results predominately in the formation of a molecule represented by structure B.

19 Claims, 18 Drawing Sheets

(56) References Cited

U.S. PATENT DOCUMENTS

| | | |
|---|---|---|
| 2,816,073 A | 12/1957 | Stratton |
| 2,861,042 A | 11/1958 | Watkins |
| 2,876,197 A | 3/1959 | Watkins |
| 2,994,660 A | 8/1961 | Reddie et al. |
| 2,999,063 A | 9/1961 | Hoeppel |
| 3,244,638 A | 4/1966 | Foley et al. |
| 4,508,628 A | 4/1985 | Walker et al. |
| 4,658,036 A | 4/1987 | Schilling |
| 6,339,048 B1 | 1/2002 | Santhanam et al. |
| 7,345,010 B2 | 3/2008 | Thompson et al. |
| 7,435,706 B2 | 10/2008 | Mueller et al. |
| 7,871,962 B2 | 1/2011 | Patel et al. |
| 8,133,970 B2 | 3/2012 | Hurd et al. |
| 8,163,675 B2 | 4/2012 | NaAvarrete et al. |
| 8,936,111 B2 | 1/2015 | Maghrabi et al. |
| 11,066,591 B2 | 7/2021 | Khramov et al. |
| 2004/0094301 A1 | 5/2004 | Hughes et al. |
| 2007/0093393 A1* | 4/2007 | Navarrete ............... C09K 23/16 507/131 |
| 2007/0167333 A1* | 7/2007 | Hurd ....................... C09K 8/72 507/244 |
| 2013/0288933 A1 | 10/2013 | Harris et al. |
| 2017/0190945 A1 | 7/2017 | Chen et al. |
| 2017/0283680 A1* | 10/2017 | Chen ....................... C09K 8/36 |
| 2018/0142134 A1 | 5/2018 | Zhou et al. |
| 2018/0142135 A1 | 5/2018 | Chen et al. |
| 2018/0148626 A1 | 5/2018 | Wagle et al. |
| 2018/0194988 A1 | 7/2018 | Hilfiger et al. |
| 2018/0223158 A1 | 8/2018 | Albahrani et al. |
| 2018/0223164 A1 | 8/2018 | Al-Yami et al. |
| 2018/0223165 A1 | 8/2018 | Wagle et al. |
| 2018/0223166 A1 | 8/2018 | Wagle et al. |
| 2018/0244975 A1 | 8/2018 | Khramov et al. |
| 2019/0233709 A1* | 8/2019 | Maghrabi ................ C09K 8/36 |
| 2020/0362221 A1 | 5/2020 | Khramov et al. |
| 2021/0323909 A1 | 10/2021 | Khramov et al. |
| 2022/0220356 A1* | 7/2022 | Khramov ............... C09K 23/22 |

FOREIGN PATENT DOCUMENTS

| | | |
|---|---|---|
| WO | 2018112450 A2 | 6/2018 |
| WO | 2018125651 A1 | 7/2018 |

OTHER PUBLICATIONS

Dolci et al., "Maleimides as a building block for the synthesis of high performance polymers", Polymer Reviews, vol. 56, No. 3, 2016, pp. 512-556.

Charville et al., "The thermal and boron-catalysed direct amide formation reactions: mechanistically understudied yet important processes", Chemical Communications, vol. 46, Issue 11, pp. 1813-1823, 2010.

Grosjean et al., "Intensified Azeotropic Distillation: A Strategy for Optimizing Direct Amidation", Organic Process Research and Development, vol. 16, Issue 5, pp. 781-787, May 18, 2012.

* cited by examiner

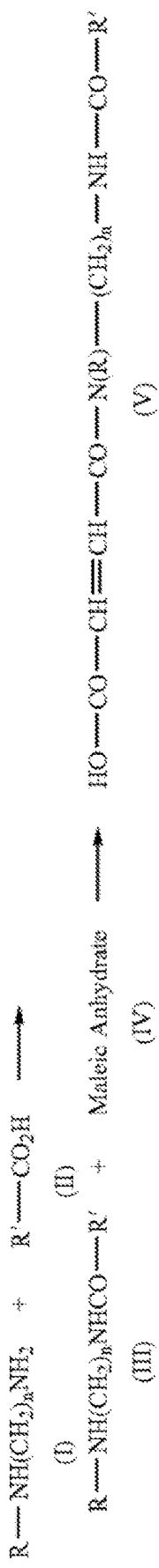
FIG. 21
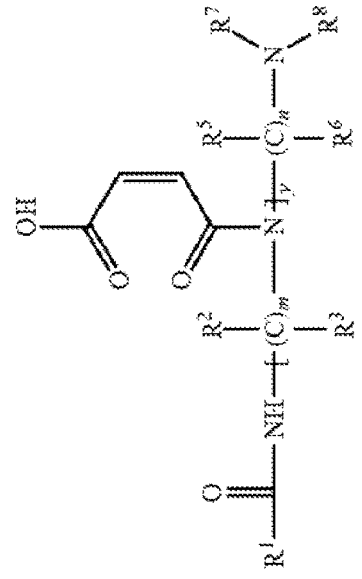
FIG. 22
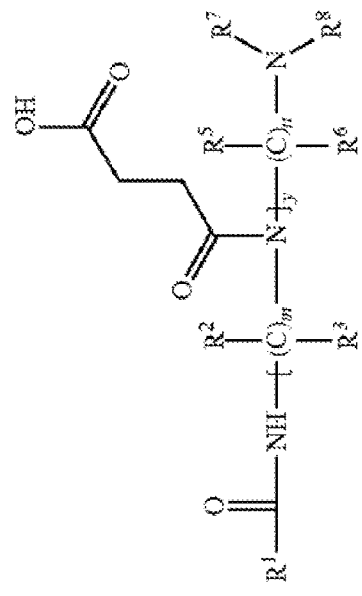

Formula I　　　　　　　　　　　　　　　Formula III

AMIDE EMULSIFIER FOR HIGH-TEMPERATURE OIL-BASED DRILLING FLUID

CROSS-REFERENCE TO RELATED APPLICATIONS

This application claims the benefit of, and priority to, U.S. Provisional Patent Application Ser. No. 63/260,398, filed Aug. 19, 2021, which application is incorporated herein by this reference in its entirety.

BACKGROUND

During the drilling of a wellbore, various fluids are typically used in the well for a variety of functions. The fluids may be circulated through a drill pipe and drill bit into the wellbore, and then may subsequently flow upward through wellbore to the surface. During this circulation, the drilling fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, to maximize penetration rate, and the like.

In many rotary drilling procedures the drilling fluid takes the form of a "mud," in which the liquid has solids suspended therein. The solids function to impart desired rheological properties to the drilling fluid and also to increase the density thereof in order to provide a suitable hydrostatic pressure at the bottom of the well. The drilling mud may be a water-based mud (WBM) or an oil-based mud (OBM).

SUMMARY

Disclosed here is a wellbore fluid. The wellbore fluid can include an oleaginous external phase, a non-oleaginous internal phase, and an emulsifier composition that includes a reaction product of a fatty amine (e.g., a primary fatty amine) and a capping agent, where the capping agent may include at least one of a cyclic anhydride or a diacid. While a primary amine works particularly well, other examples may possibly employ other types of amines (e.g., a secondary amine). Such a primary fatty amine is characterized by the classic definition of primary amine, i.e., a structure where the nitrogen of the amine group is bonded to a single carbon atom (the other atoms bonded to the nitrogen are hydrogens). Such a primary fatty amine may include one or more amine groups (e.g., a diamine, triamine, etc.). The primary fatty amine can be unsaturated (i.e., includes at least a single carbon-carbon double bond). Such emulsifiers and associated wellbore fluids are particularly useful in the context of invert emulsion wellbore drilling fluids, e.g., providing alternatives to existing amido-amine based emulsifiers. Such emulsifiers and associated wellbore fluids provide a benefit of being relatively simple and easy to produce compared to existing solutions, while also providing increased tunability as to important performance characteristics, such as hydrophobic-lipophilic balance (HLB). For example, HLB of the resulting emulsifier may be adjusted by adjusting the carbon chain length of the primary fatty amine used in the reaction.

The primary fatty amine may have an alkyl chain length of 12 to 70 carbons. For example, the primary fatty amine can include one or more of oleyl amine, linoleyl amine, tall oil amine, or tallow amine (e.g., glyceryl esters of fatty acid chains having 16-18 carbons). A possible capping agent is a cyclic anhydride, such as, but not limited to maleic anhydride, succinic anhydride, alkenyl succinic anhydride, alkyl succinic anhydride, glutaric anhydride, or phthalic anhydride. Diacids can also be used as capping agents. The reaction product can be formed at a temperature of from 60° C. to 80° C. In another possibility, the reaction product can include a Structure A formed at a temperature from 60° C. to 80° C., and/or a Structure B formed at a temperature of from 100° C. to 180° C. In some examples, Structure A includes an internal, non-terminal amide group derived from the amine of the primary fatty amine and a carboxyl group of the cyclic anhydride or diacid capping agent. Structure A can further include a terminal or free carboxylic acid group derived from another carboxyl group of the cyclic anhydride or diacid capping agent. As such, structure A can be an amic acid. The nitrogen atom in such a Structure A can be positioned towards the fatty chain provided by the primary fatty amine (e.g., between the carboxyl group of the amide group, and the fatty chain), rather than on the other side of the carboxyl group of the amide group, towards the terminal end of Structure A. Such positioning of the nitrogen atom differentiates Structure A from superficially similar appearing emulsifiers, such as oleoyl sarcosine (HAMPOSYL O).

Structure B can be derived from Structure A, by further heating of Structure A, resulting in a Structure B that includes a terminal cyclic group (e.g., formed as a result of ring closing of the amide and free carboxylic acid groups of Structure A). In a possibility, the reaction conditions are controlled to favor production of the emulsifier of Structure A, for example, by maintaining reaction conditions below 100° C., below 90° C., below 85° C., or no greater than 80° C. (e.g., from 60° C. to 80° C.). Where temperatures are elevated (e.g., above 80° C.), such as 100° C. to 180° C.), a mixture of Structures A and B may result. While Structures B can provide suitable emulsifiers, Structure A may provide more efficient emulsification of oleaginous and non-oleaginous phases.

Rheology modifying additives can be added, examples of which include, but are not limited to one or more of fatty acids, dimers, trimers, other oligomers, fatty acid dimers, fatty acid trimers, alcohol ethoxylates, or combinations thereof such as RHECON or hexyl CARBITOL series additives.

Another aspect of the present disclosure relates to a wellbore fluid including an oleaginous phase (e.g., the external phase), a non-oleaginous phase (e.g., the internal phase), one or more rheology additives, and an emulsifier of generic formula A or B or A+B, which emulsifier is a reaction product of a primary fatty amine and a capping agent, where the capping agent includes one or more of a cyclic anhydride, an alpha-halo carboxylic acid, a monoester of a dicarboxylic acid, or a cyclic sulfonate ester.

Another aspect of the present disclosure relates to a wellbore fluid emulsifier that includes a reaction product of primary fatty amine and a capping agent including one or more of a cyclic anhydride, or a diacid.

In some examples, the reaction forming the reaction products forms a blend of Structure A and Structure B components. By way of example, the capping agent can be succinic anhydride, and the resulting reaction product (an example of Structure A) can include the below compound.

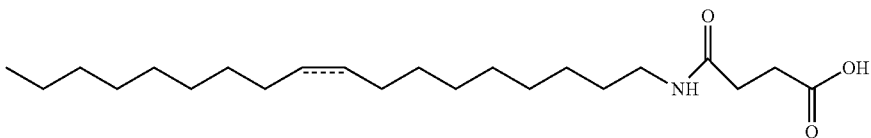

As will be apparent, Structure A includes an internal, non-terminal amide group derived from the amine of the primary fatty amine and a carboxyl group of the succinic anhydride. Structure A further includes a terminal or free carboxylic acid group derived from the other carboxyl group of the succinic anhydride. In other words, Structure A is an amic acid. The nitrogen atom in the above example of Structure A is positioned towards the fatty chain provided by the primary fatty amine, relative to the carboxyl group of the resulting amide group. This placement of the nitrogen atom differs from placement seen in existing wellbore fluid emulsifiers, such as oleoyl sarcosine (HAMPOSYL O).

In some examples, the reaction product can include the below compound, which is an example of Structure B, derived from the above Structure A.

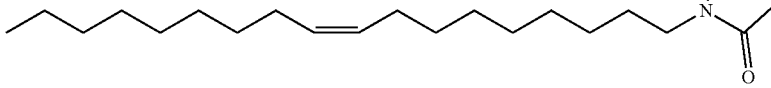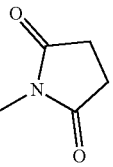

By way of further explanation, Structure B including a terminal cyclic group shown above may be, formed at relatively higher temperature (e.g., from 100° C. to 180° C.), while the linear structure shown above which is exemplary of Structure A, forms at a relatively lower temperature (e.g., from 60° C. to 80° C.). In some examples, Structure A may be a more efficient emulsifier, such that temperatures and/or other reaction conditions may be maintained to favor production of such linear structures over the Structure B compound including a terminal cyclic structural group (e.g., a cyclic imide), which results at higher temperatures.

Another aspect of the present disclosure relates to a method for forming a wellbore fluid emulsifier, the method including the steps of forming a mixture of a primary fatty amine, such as oleyl amine with a cyclic anhydride such as succinic anhydride, heating the mixture, and including the mixture in a wellbore fluid having oleaginous and non-oleaginous phases. By way of example, forming such a mixture may include combining substantially equimolar amounts of the primary fatty amine (e.g., oleyl amine) and the cyclic anhydride (e.g., succinic anhydride). Forming the mixture may further include the addition of a suitable solvent or diluent (e.g., oil diluent), such as dodecane.

Heating the mixture may include heating to a first maximum temperature between 60° C. and 100° C., and holding such temperature for a first period of time. A method may include heating the mixture to a second temperature greater than the first maximum temperature, and holding the mixture at such second temperature for a second period of time. Additional heating can also be performed (e.g., heating the mixture to a third temperature greater than the second temperature, and holding the mixture at such third temperature for a third period of time). In some examples, the second time period can be longer than the third time period, and the third time period longer than the first time period. Heating such mixture can include a first stage (e.g., at the first temperature) that forms a reaction product having a Structure A. Heating the mixture can include a second stage (e.g., at the second temperature) that forms a reaction product having a Structure B. The Structure B may be a derivative of Structure A, but including a terminal cyclic group (e.g., a cyclic imide).

BRIEF DESCRIPTION OF THE DRAWINGS

FIGS. 12-1 and 12-2 are charts of Gel-Permeation Chromatography (GPC) data of two compounds occurring during stages of emulsifier synthesis, in tetrahydrofuran (THF), according to an embodiment of the present disclosure;

FIG. 21 is a synthesis route for a polyamide emulsifier, according to some embodiments of the present disclosure;

FIG. 22 shows formulas of emulsifiers, according to some embodiments of the present disclosure;

DETAILED DESCRIPTION

Compositions of the present disclosure can include stabilizing wellbore fluid formulations, including invert emulsion drilling and other wellbore treatment fluids. In at least some embodiments, compositions include amide and/or cyclic imide-based emulsifiers. Emulsifiers in accordance with the present disclosure may be used to prepare emulsified wellbore fluids, including water-in-oil or invert emulsions in which an aqueous internal phase is stabilized by an emulsifier in an oil continuous phase.

Figure 1:
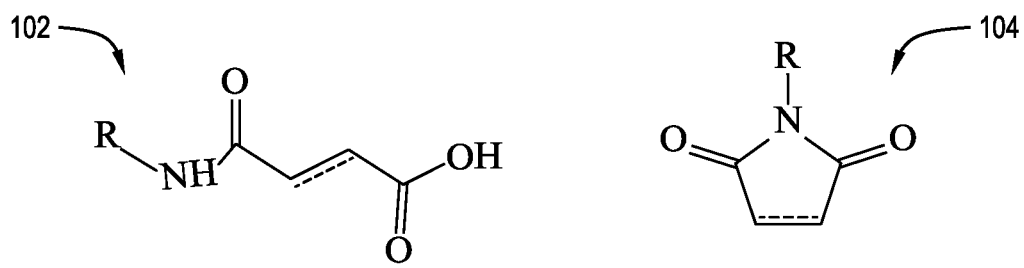
FIG. 1 shows generic formulas (Structures A and B) for emulsifier compounds that include an amide group and a terminal or free carboxylic acid group (Structure A) as well as a cyclic imide (Structure B), according to an embodiment of the present disclosure (the broken lines shown in the Structures A and B of FIG. 1 indicate that such bonds may be single or double bonds)

Example drilling fluid compositions according to the present disclosure include an oil medium (oleaginous external phase), an aqueous phase (non-oleaginous internal phase), and an emulsifier composition having a generic structure that includes structure 102 (Structure A), structure 104 (Structure B), or a combination of structures 102 and 104 as shown in FIG. 1. The emulsifier composition includes an amide 102, a cyclic imide 104, or a mixture thereof. The broken lines shown in Structures A and B of FIG. 1 indicate that such bonds may be single or double bonds, e.g., derived from succinic anhydride or maleic anhydride, respectively). The emulsifier of the emulsifier system is formed by reacting a fatty oil amine (e.g., oleyl amine) with a cyclic anhydride (e.g., succinic anhydride). The emulsifier may be formed in solvent-free conditions (i.e. in the absence of diluent), although in other embodiments formation may occur in a diluent, such as a diluent that will not react with either of the starting materials. An unreactive diluent can include a base oil such as IO1618, an alkane such as dodecane, or an alkane mixture.

Figure 2:
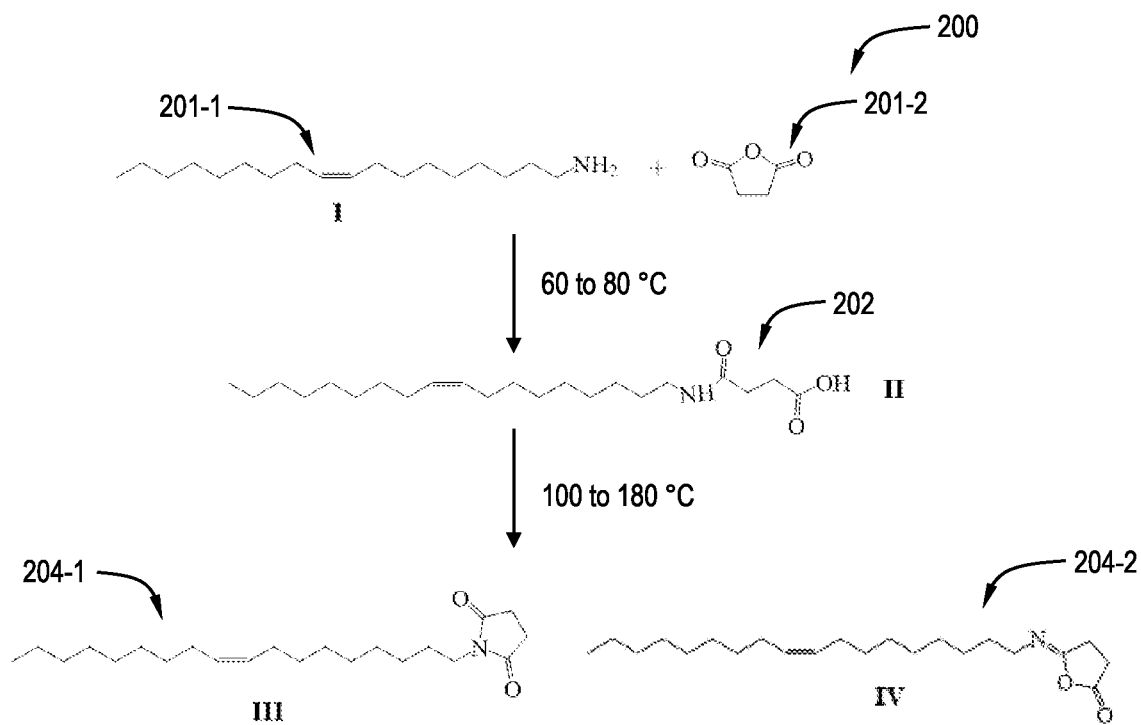
FIG. 2 is a method of preparing an emulsifier by reacting oleyl amine with succinic anhydride, according to an embodiment of the present disclosure.

The reaction may take place by applying increasing temperature. For instance, a process 200 as shown in FIG. 2 may be used, in which a stepwise increase in temperature is applied to prepare an emulsifier using a reaction between oleyl amine 201-1 and succinic anhydride 201-2. An emulsifier 202 based on structure 102 of FIG. 1 (an amide) can form when the reaction temperature is maintained at one temperature (e.g., at 60 to 80° C.) for a period of time (e.g., for 1 to 3 hours). A further increase in reaction temperature (e.g., to about 100 to 180° C.) can then occur, and water can be eliminated, which results predominately in the formation of compound 204-1, and optionally compound 204-2, at least one of which can be represented by the cyclic imide structure 104 of FIG. 1 (e.g., structure 204-1), while another may be a related by-product (e.g., structure 204-2).

In accordance with some aspects, emulsifier compositions (including those formed as discussed herein), may be appropriate with a wellbore fluid having a flat rheology profile. As used herein, the term "flat rheology profile" means that substantially consistent rheological properties are maintained over a temperature range spanning between 40° F. (4° C.) and 150° F. (66° C.). Such emulsifier compositions can be based on the reaction product of a primary fatty amine (e.g., oleyl amine 201-1 in FIG. 2) and various cyclic anhydrides (e.g., succinic anhydride 201-2 in FIG. 2).

Figure 3:
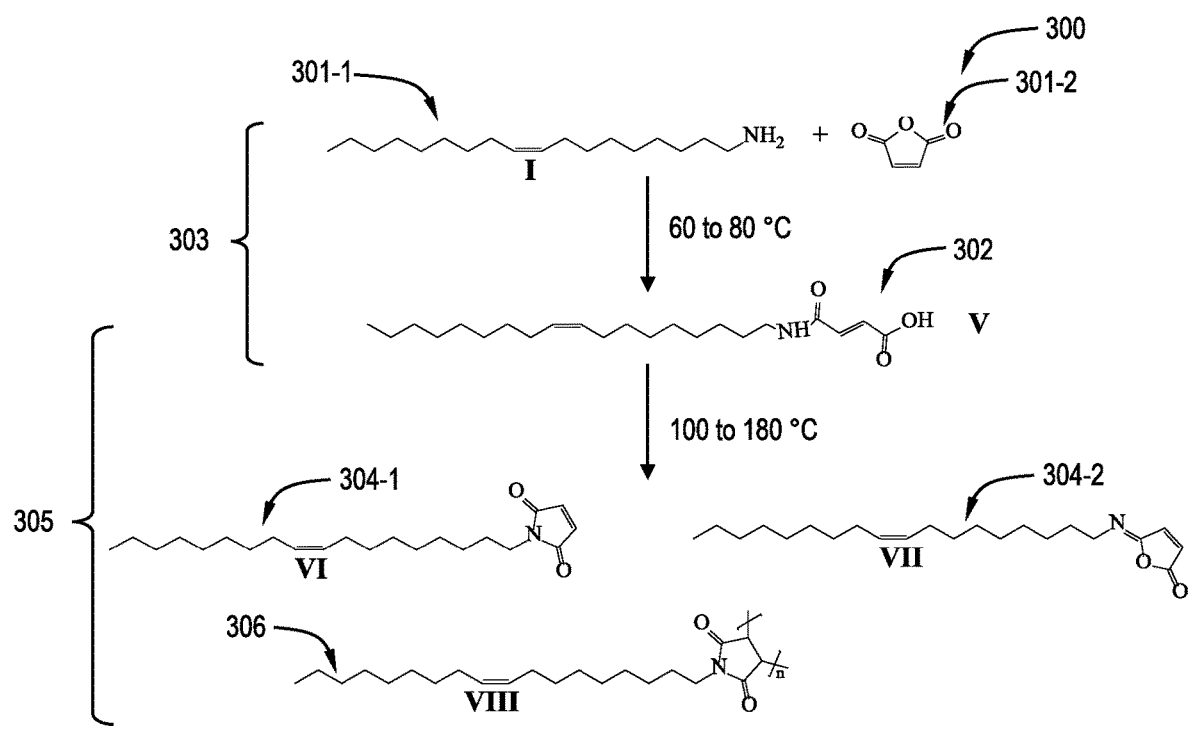
FIG. 3 is a method for preparing an emulsifier by reacting oleyl amine with maleic anhydride, according to an embodiment of the present disclosure.

In other embodiments, other or additional anhydrides could be used. For instance, FIG. 3 illustrates a similar process 300, in which maleic anhydride 301-2 is reacted with oleyl amine 301-1. In still other embodiments, other anhydrides (e.g., itaconic, glutaric, (2-dodecen-1-yl)-succinic, phthalic, etc.) may be used. Additionally, while the anhydrides used in embodiments of the present disclosure may be cyclic, they are not cyclic in other embodiments. However, commercially available anhydrides are typically cyclic. In further embodiments, the emulsifier is terminated with a free carboxylic acid group, which the applicant has found correlates with improved performance. In at least some embodiments, preparation of a more simple amide (e.g., the reaction product of oleyl amine and acetic anhydride), has reduced performance.

In a further aspect, embodiments of the present disclosure relate to methods of manufacturing an emulsifier, including methods such as those generally depicted in FIGS. 2 and 3 for synthesizing structures (e.g., structures of the generic form 102 and 104 of FIG. 1). For instance, reactions can be performed under stoichiometric conditions (e.g., one mole of oleyl amine 201-1 is reacted with one mole of succinic anhydride 201-2 in FIG. 2). The process illustrated in FIG. 2 provides a general pathway for the formation of (Z)-4-(octadec-9-enylamino)-4-oxobutanoic acid 202 and (Z)-1-

(octadec-9-enyl)pyrrolidine-2,5-dione 204-1, with reaction conditions and product composition described in more detail in Example 1.

FIG. 3 shows general a pathway for the formation of an emulsifier via a reaction between one mole of oleyl amine 301-1 and one mole of maleic anhydride 301-2, resulting in the formation of the maleamic acid derivative 302 and maleimide 304-1. As shown, the maleamic acid derivative 302 may be a maleamic acid compound, where one of the hydrogen atoms bonded to the nitrogen of the amide group has been replaced by the fatty chain of the primary fatty amine. Reaction conditions and product composition are described in more detail in Example 2. The reaction of the method 300 is performed in two steps 303, 305.

The first step 303 includes forming maleamic acid derivative 302 ((E)-4-((Z)-octadec-9-enylamino)-4-oxobut-2-enoic acid) via a ring-opening reaction between maleic anhydride 301-2 and a primary amine (e.g., oleyl amine 301-1). The reaction temperature during the first step 303 can be maintained within a desired range, such as between 60 and 80° C. (e.g., 70° C.) for a desired time period such as 1 to 3 hours (e.g., 2 hours). In the same or other embodiments, the time period can be based on one or more of determining that the residual oleyl amine concentration is reduced or by measuring the amine number. For instance, the time period may end when the residual oleyl amine concentration is determined to be less than the detection limit of the $^1$H NMR spectroscopy method, or the amine number is measured in non-aqueous media to be less than 1 mg KOH/g.

The second step 305 can include intramolecular cyclization of the maleamic acid derivative 302. The condensation reaction between the amide and the terminal carboxylic acid group can be carried out with a specific catalyst. The reaction products formed during the second step 305 can be dependent on temperature. By choosing the specific conditions used, the method 300 can control a ratio of formed maleimide compound 304-1 and a by-product iso-maleimide 304-2. In at least some embodiments of the present disclosure, the second step 305 is performed at a second temperature. The second temperature may be less than or greater than the temperature of the first step 303. In the illustrated method 300, the temperature in the second step 305 is greater than that in the first step 303. For instance, the temperature may be between 100 and 180° C. (e.g., 140° C.).

The synthesis of emulsifiers with structure 102 (e.g., structures 202 and 302) can be performed in bulk, such as in solvent-free conditions. Alternatively, a high boiling point solvent can be used, such as a base oil IO1618 or an alkane (e.g., dodecane) and an acid catalyst. Similar solvents can be used for a second production step to produce structure 104 (e.g., 204-1 and 304-1 or 304-2). Water formed during the reaction can be removed, such as using a Dean-Stark apparatus or in nitrogen flow. Additional or alternative methods to remove water can also be used and are within the scope of the present disclosure.

The second step 305 of the reaction 300 between oleylamine and maleic anhydride in FIG. 3 can be accompanied by continuous dimerization/oligomerization of the maleimide derivative 306, as shown in FIG. 3. Substituted maleimides can be strong electron-accepting monomers and can react in three different ways, including: nucleophilic reaction (Michael addition typically with an amine or thiol, homo-polymerization); cycloaddition (Diels-Alder reaction); and radical reaction (homo-polymerization and co-polymerization). Substituted maleimides could polymerize under thermal or photochemical stimulation. Thermal polymerization of maleimide derivatives may require an initiator, such as Azobisisobutyronitrile (AIBN). Maleimide derivatives can also co-polymerize with a donor monomer to produce alternating copolymers through a free radical mechanism, which can include using either a thermal or UV-based process.

In some further embodiments, alternative methods to synthesize an emulsifier composition are based on the thermal treatment of an acid (e.g., carboxylic acid) and an amine (e.g., in the absence of catalyst). Such a reaction may have a reaction temperature between 100 and 180° C. (e.g., 140° C.). Further, it has been determined that a significant amount of the amide product can be formed even at lower temperature, usually when coupled with azeotropic removal of water. The yield of the thermal amidation reaction may be highly dependent on the substrate, and also dependent on temperature, substrate concentration, solvent, and other reaction parameters. In some cases, this alternative method based on thermal treatment of an acid and amine in the absence of a catalyst may require an elevated reaction temperature and may cause increased contamination of the emulsifier with by-products (decreased yield), as compared to the methods of FIGS. 2 and 3.

Catalysts (e.g., lipases) can be used to reduce temperature of the formation of primary amides from carboxylic acids and amines. In some embodiments, such catalysts are critical as maleic anhydride capping agents. In some cases, both the intramolecular cyclization of the maleamic acid derivative 302 such as maleimide 304-1 and iso-maleimide 304-2, as well as the dimerization/oligomerization of the maleimide product 306, may be undesirable for certain emulsifiers of this present disclosure and could lead to a deterioration in the rheological properties of an oil-based mud (OBM) formulation. Significantly, however, these structures may be useful for other oilfield applications, such as for use as viscoelastic surfactants in the recovery of hydrocarbons/fracturing or acid stimulation.

In further aspects of the present disclosure, amide groups can also be formed from amines and pre-activated carboxylic acid derivatives, such as acid chlorides (using thionyl or oxalyl chloride) or by using the carboxylic acid directly with a coupling reagent such as carbodiimide. At present, these approaches may be less cost effective as compared to cyclic anhydride methods discussed herein.

In methods of synthesizing desired structures, primary fatty amines can be completely converted into their corresponding amides when treated with the acid esters (e.g., mono-esterified dicarboxylic acids such as mono-methyl fumarate, adipic acid monomethyl ester, etc.). The reaction can take place without solvent or any other reagents in some embodiments, and can take place when the reaction is maintained at 40 to 80° C.

It is also noted that when the thermal reaction between primary fatty amines and cyclic anhydrides is performed under controlled temperature conditions (e.g., 60 to 80° C.), the targeted amide product (e.g., generically product 102 of FIG. 1) can be produced with high quality in terms of purity. Additionally, such processes may utilize only basic synthesis equipment and have a reduced process time relative to various other approaches.

To further illustrate examples of the present disclosure, various examples have been prepared, with a series of amic acids (e.g., structures 102) and corresponding cyclic imides (structures 104). These examples include reacting oleyl amine with the appropriate cyclic anhydride as shown in Table 1, which shows emulsifiers formed based on reactions between oleyl amine and various anhydrides (capping agents). (2-dodecen-1-yl) succinic anhydride is an example of the more general class of alkenyl succinic anhydrides, any of which may be suitable for use herein. Similarly, methyl succinic anhydride an example of the more general class of alkyl succinic anhydrides, any of which may be suitable for use herein.

TABLE 1

| Capping agent | Amide | Imide |
| --- | --- | --- |
| Succinic anhydride | Ex. 1 | Ex. 2 |
| (2-Dodecen-1-yl)succinic anhydride | Ex. 3 | Ex. 4 |
| Maleic anhydride | Ex. 5 | Ex. 6 |
| Glutaric anhydride | Ex. 7 | — |
| Phthalic anhydride | — | Ex. 8 |
| Methyl succinic anhydride | — | — |

Figure 4:
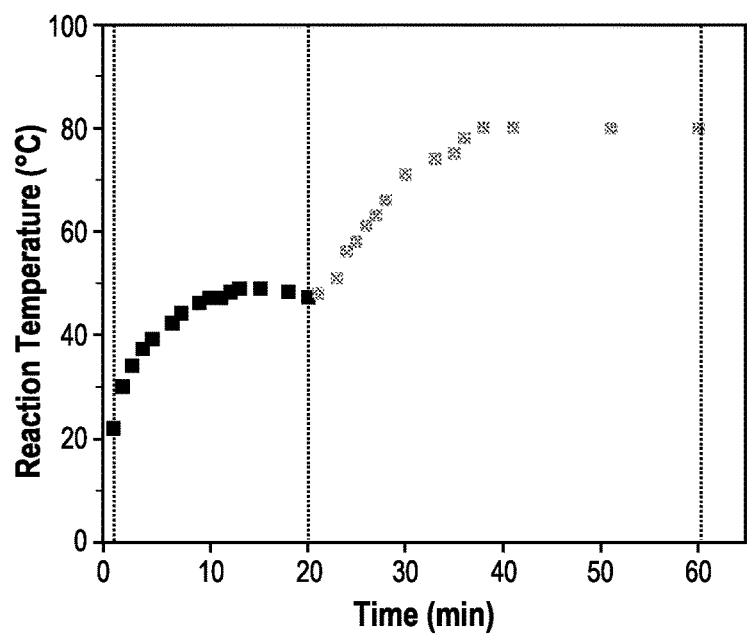
FIG. 4 is a chart showing temperature conditions during a first step of a reaction between oleyl amine and succinic anhydride in dodecane, according to an embodiment of the present disclosure.

Example 1: Synthesis of Emulsifiers Ex. 1 and Ex. 2 Via Reaction of Oleyl Amine with Succinic Anhydride In this example, a synthesis process was used that is similar to the method 200 as shown in FIG. 2. In a first step, Ex. 1 (product 202) is synthesized. Specifically, in a two-necked glass flask equipped with a thermometer and a magnetic stirrer, 140 g of oleyl amine, and 192.372 g of dodecane was mixed at room temperature with 52.372 g of succinic anhydride powder. Equimolar amounts of reactants were used. The temperature inside the flask was recorded and is shown in FIG. 4.

As shown, the reaction temperature began at 22° C. and rose spontaneously in a self-heating, exothermic reaction over 20 minutes, when it stabilized at 47° C. A hotplate used as the heating element was then turned on and set to 80° C., and the reaction temperature reached 80° C. over the next 20 min. The reaction continued at 80° C. for another 20 minutes, and then stopped at a total reaction time of 1 hour. The purity of amide, (Z)-4-(octadec-9-enylamino)-4-oxobutanoic acid (Ex. 1) was monitored by nuclear magnetic resonance (NMR) and Fourier-transform infrared (FTIR) spectroscopy.

In the second step of the process, Ex. 2 (product 204-1) is synthesized. This portion of the process includes heating the reaction mixture produced during first step (Ex. 1) to a temperature of 120° C. for 21 hours, and then the temperature was increased to about 140° C. for 4 hours. This heating was performed under constant nitrogen flow. It was observed that the product changed from a pale cream to red-brown color. The purity of cyclic imide (Z)-1-(octadec-9-enyl) pyrrolidine-2,5-dione (Ex. 2) was confirmed by NMR and FTIR spectroscopy.

Figure 5:
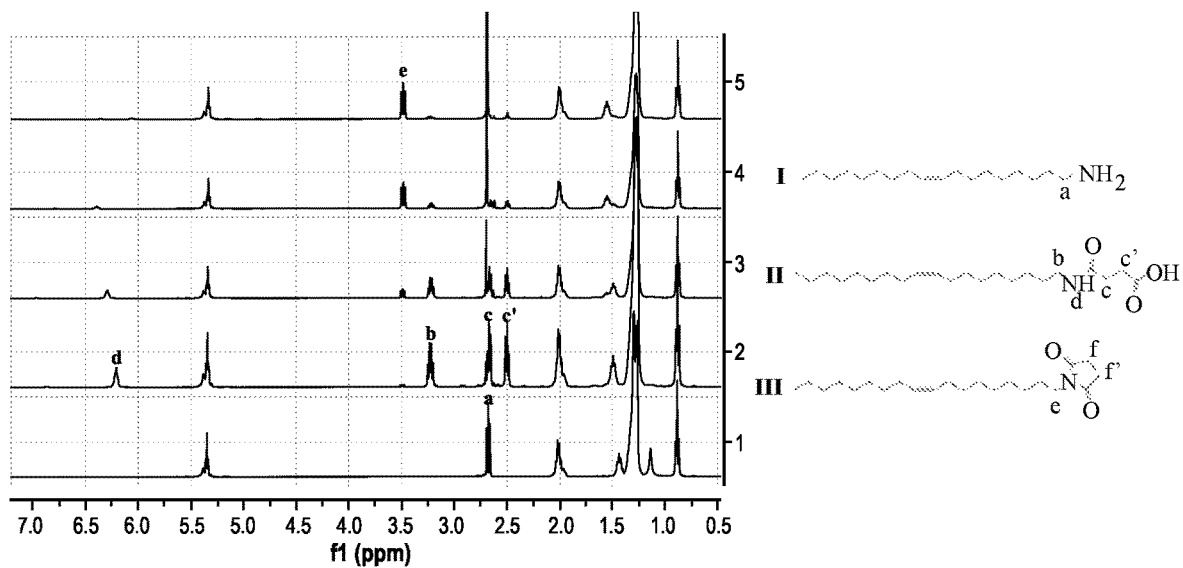
FIG. 5 is a chart of $^1$H NMR spectra during synthesis of an emulsifier produced in one example, according to an embodiment of the present disclosure.
Figure 6:
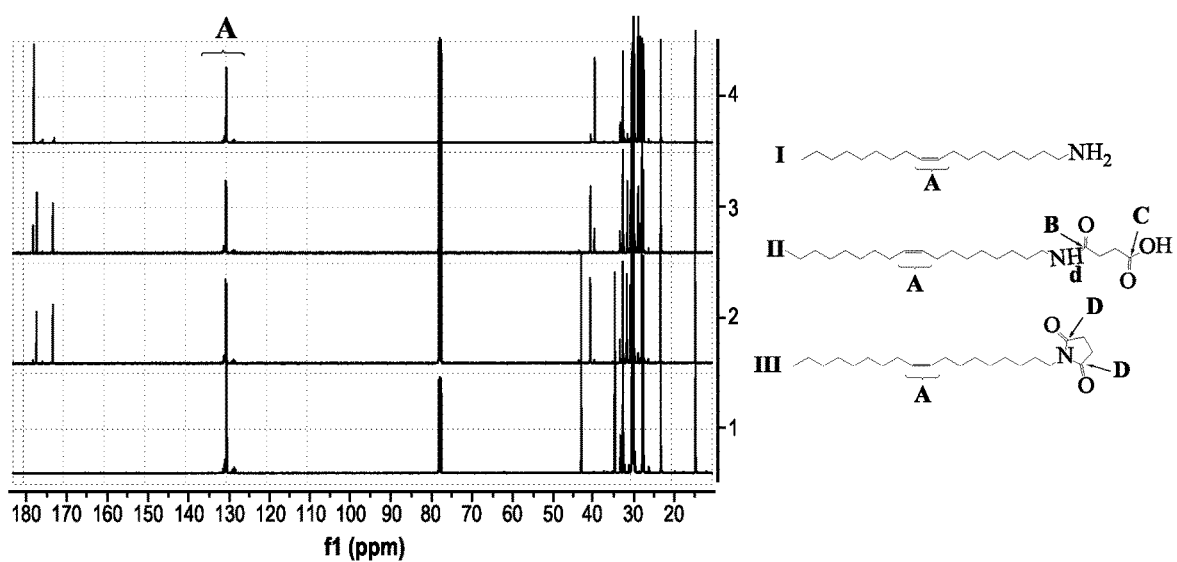
FIG. 6 is a chart of $^{13}$C NMR spectra during the synthesis of the example of FIG. 5, according to an embodiment of the present disclosure.

In particular, FIG. 5 illustrates $^1$H NMR spectra of compound I (oleyl amine) in spectrum 1, compound II ((Z)-4-(octadec-9-enylamino)-4-oxobutanoic acid (Ex. 1)) in spectrum 2, and compound III ((Z)-1-(octadec-9-enyl) pyrrolidine-2,5-dione (Ex. 2)) in spectrum 5. Compound II was synthesized in the first step of the process, and compound III (Ex. 2) was obtained in the second step by stepwise aging of compound II (Ex. 1) at 110° C. for 2 hours (see spectrum 3), 17 hours (see spectrum 4), and at 140° C. for 7 hours for the result in spectrum 5. FIG. 6 illustrates $^{13}$C NMR spectra of compound I in spectrum 1, compound II (Ex. 1) in spectrum 2, and compound III (Ex. 2) in spectrum 4. Compound III (Ex. 2) was obtained by stepwise aging of compound II (Ex. 1) at 110° C. for 2 hours (see spectrum 3) and at 140° C. for 7 hours to obtain the result in spectrum 4.

Figure 7:
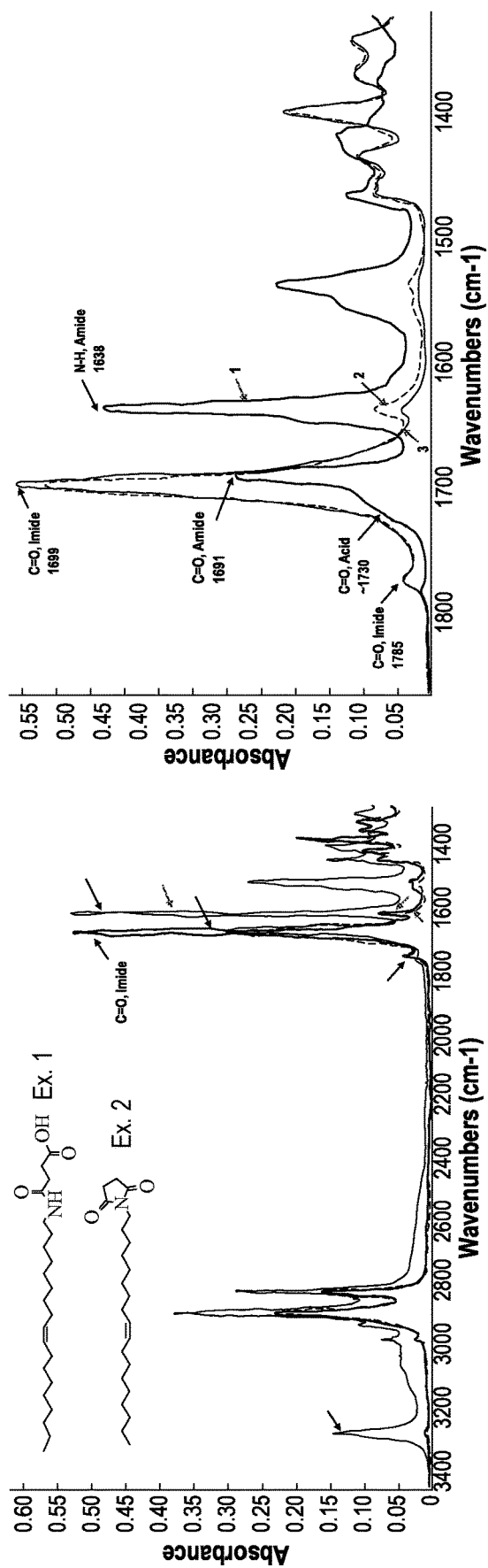
FIG. 7 is FTIR spectra of the synthesis of the example compound of FIGS. 5 and 6, according to an embodiment of the present disclosure.

FIG. 7 illustrates FTIR spectra of compound II (Ex. 1) in line/spectrum 1 and compound III (Ex. 2) in line/spectrum 3. Compound II (Ex. 2) was obtained by stepwise aging of compound II (Ex. 1) at 110° C. for 17 hours (see spectrum 2), and at 140° C. for 4 hours to obtain the result in line/spectrum 3. Notably, in performing the reaction according to these conditions, no significant by-product was produced.

Figure 8:
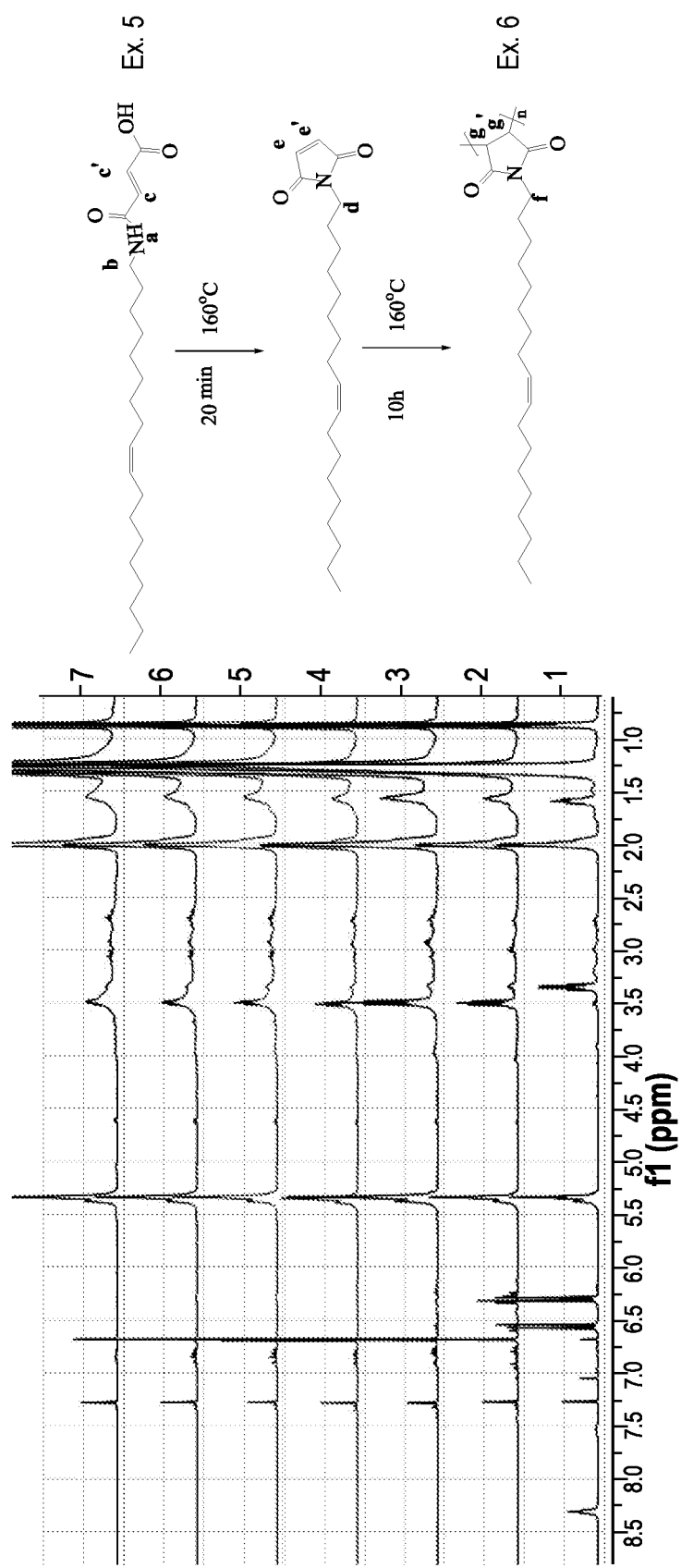
FIG. 8 is a chart of $^1$H NMR spectra of compound(s) and aging of those compound(s) for various periods of time, according to an embodiment of the present disclosure.

Example 2: Synthesis of Emulsifiers Ex. 5 and Ex. 6 by Reacting Oleyl Amine with Maleic Anhydride In this example, a synthesis process was used that is similar to the synthesis method 300 as shown in FIG. 3. In a first step, Ex. 5 (e.g., product 302) is synthesized. Specifically, in a two-necked flask equipped with a thermometer and magnetic stirrer, 70 g of oleyl amine, and 25.66 g of maleic anhydride powder were mixed at room temperature. Equimolar amounts of oleyl amine and maleic anhydride were used, and no solvent was used. The reaction mixture was stirred for 2 hours at 70° C. (±2° C.) to avoid overheating of the system. The purity of the resulting maleimide was monitored by NMR and FTIR spectroscopy (see FIGS. 8 to 10). In particular, the $^1$H NMR chemical shift of typical maleimide protons c, c' appear as two doublets at 6.31 ppm and 6.55 ppm (FIG. 8).

Figure 9:
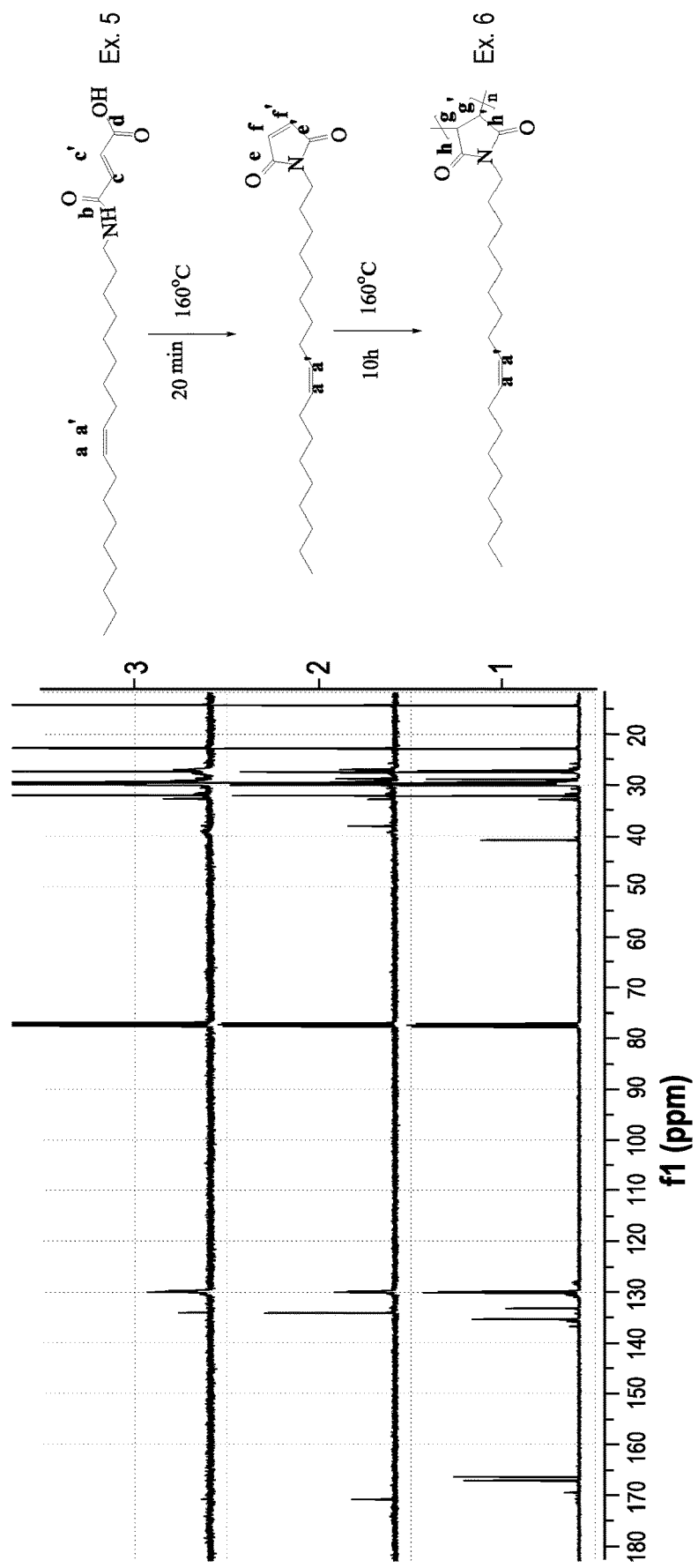
FIG. 9 is a chart of $^{13}$C NMR spectra of compound(s) and aging of those compound(s) for two periods of time, according to an embodiment of the present disclosure.
Figure 10:
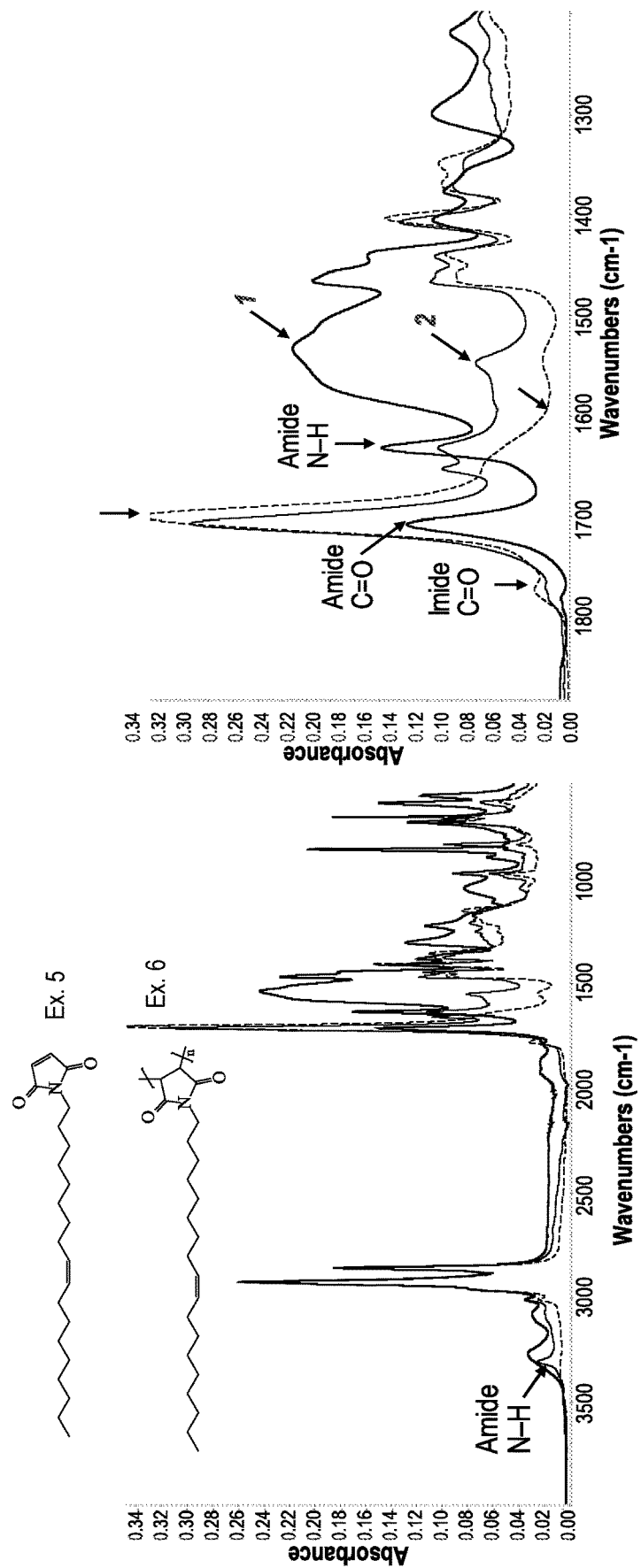
FIG. 10 is FTIR spectra of the synthesis of the example compound(s) of FIGS. 8 and 9, when aged for various periods of time, according to an embodiment of the present disclosure.

In the second step of the process, Ex. 6 is synthesized, which includes the synthesis of maleimide (e.g., product 304-1) and poly(maleimide) (e.g., product 306) is as follows: 70 g of oleyl amine and 25.66 g of maleic anhydride powder was mixed at room temperature and then heated at 160° C. for 10 h under nitrogen flow. The maleimide formed very quickly, and is further understood by referring to FIG. 8. In particular, FIG. 8 illustrates the $^1$H NMR spectra of unaged Ex. 5 in spectrum 1. Spectrums 2 to 7 illustrate the spectra after the Ex. 5 has aged at 160° C. for 20 minutes (spectrum 2), 1 hour (spectrum 3), 2 hours (spectrum 4), 4 hours (spectrum 5), 5 hours (spectrum 6), and 10 hours (spectrum 7). As shown, the NMR spectrum of the reaction at a time of 20 minutes (see spectrum 2) shows that the characteristic protons of maleimide (two doublets at 6.31 and 6.55 ppm) begin to disappear, and the typical maleimide protons e, e' appear as a singlet at 6.69 ppm. FIG. 9 is a $^{13}$C NMR spectra of the Ex. 5 compound in spectrum 1, and during aging at 160° C. for 20 minutes (spectrum 2) and after 10 hours (spectrum 3). FIG. 10 is a FTIR spectra of Ex. 5 in spectrum 1, and during aging at 160° C. after 16 min (spectrum 2) and after 5 hours (spectrum 3).

Figure 11:
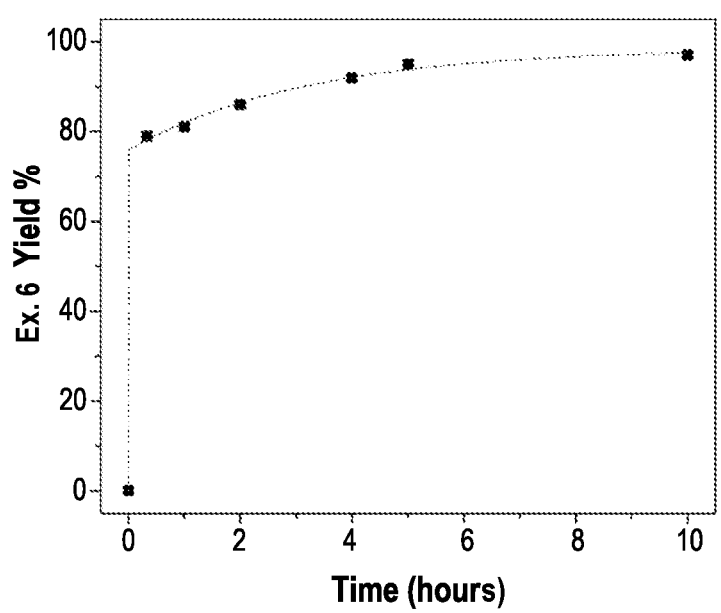
FIG. 11 is a chart showing the conversion yield for an emulsifier compound versus time, according to an embodiment of the present disclosure.

At the reaction temperature of 160° C., it is difficult if not impossible to obtain pure maleimide. Analysis of the integral at 6.69 ppm shows that the reaction product at a time of 20 minutes includes a mixture of 20% maleimide and 80% poly(maleimide). The yield of conversion of maleimide to poly(maleimide) as a function of reaction time is shown in FIG. 11. In FIG. 11, the conversion yield of Ex. 5 to Ex. 6 at 160° C. is shown versus time. In this case, the concentration of Ex. 6 was estimated using an analysis of the integral at 6.69 ppm (—CH=CH—, maleimide) shown in FIG. 8.

Figures 2, 12:
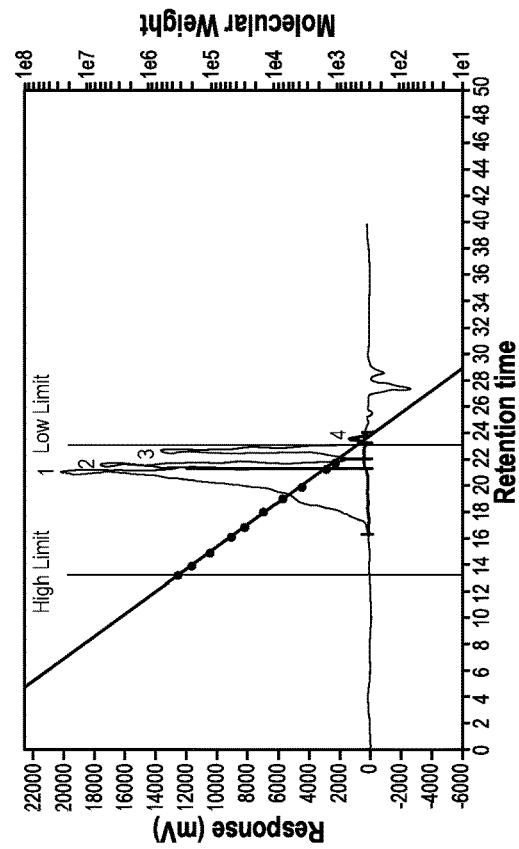
Figures 1, 12:
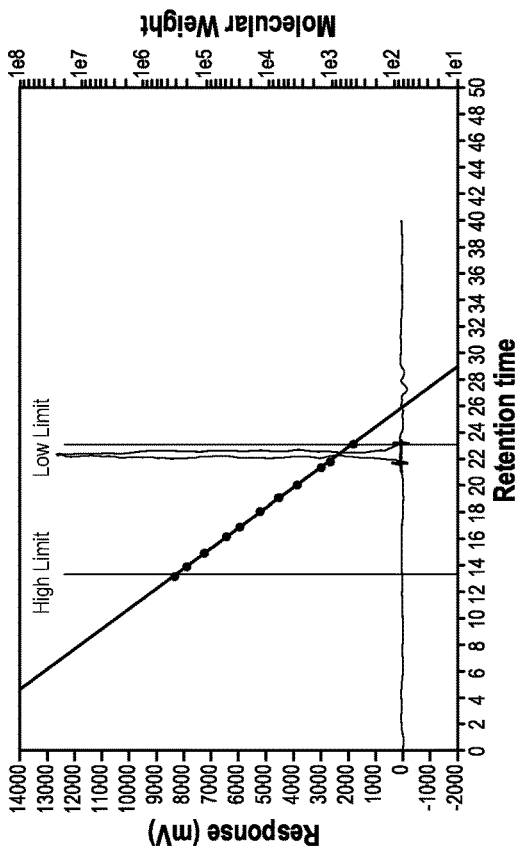

According to NMR analysis, the product Ex. 6 is 97% of poly(maleimide). Gel-permeation chromatography (GPC) data of Ex. 5 is shown in FIG. 12-1. GPC data of Ex. 6 obtained using stepwise aging of Ex. 5 at 150° C. for 15 hours and at 160° C. for 2 hours is shown in FIG. 12-2. In both cases, polystyrene standards were used (data points and connecting, diagonal line) for calibration. The GPC data in FIGS. 12-1 and 12-2 also confirm the formation of a high molecular weight product, with FIG. 12-2 showing Ex. 6 had an average molecular weight of 4,152 as compared to a. average molecular weight of 809 for Ex. 5 as shown in FIG. 12-1. Such values may represent weight average molecular weights.

The reaction outlined and generally depicted in FIG. 3 is operationally simple to perform, and progresses quite rapidly. Indeed, it can go to completion in less than 1 hour at 80° C. in some embodiments. Conceptually, this process may be similar to that described in U.S. patent application Ser. No. 16/636,017, which was filed on Feb. 2, 2020, although this process should be monitored frequently for progress of the reaction, and the reaction should be conducted at the correct temperature. Such application is herein incorporated by reference in its entirety.

Example 3: Mud Formulation and Performance

Several synthetic-base mud (SBM) formulations are shown below in Tables 2 to 6. Each SBM formulation was prepared using additives, and emulsifier formulations are summarized in Table 1. The properties of the formulated mud were evaluated using a conventional approach for mud property analysis. The properties of the mud after heat stress were evaluated by studying the rheology of the mud using a FANN 35 viscometer. The measurements were performed after mud preparation and after mud aging at 325° F. (163° C.) in a roller oven for 16 hours.

TABLE 2

SBM Formulation

| Component | Mass (g) |
| --- | --- |
| AMORDRIL 1000 | 139 |
| Emulsifier | 12 |
| RHECON | 4 |
| SUREWET | 1.5 |
| VG 69 | 0.5 |
| Lime | 5 |
| 25% CaCl$_2$ Brine | 77.3 |
| DURAMOD | 13 |
| ECOTROL HT | 0.75 |
| SUREMOD | 2.13 |
| Micronized barite | 351 |

Table 2 specifically shows an example SBM formulation, and Table 3 shows the rheology and HPHT properties of the SBM formulation prepared using emulsifiers Ex. 1, Ex. 2, Ex. 5, and Ex. 6. In this case, the mud is a 14.19 ppg oil-based mud (OBM) having an oil-to-water ratio of 78:22.

In Table 3, Ex. 1 is amide emulsifier prepared according to the desired specifications, and has desirable parameters such as R600 @ 40° F., 3/6 rpm @ 150° F., and low HPHT fluid loss. Low 40/150° F. gels demonstrated in this formulation also have good results, while achieving low gel strength while boosting 3/6 rpm values has been a very challenging step in SBM developments.

Table 3 also shows the rheological profile for Ex. 2 emulsifier (imide derivative) made from the same raw materials used to make Ex. 1. In this case, the emulsifier was prepared at an elevated temperature (120 to 140° C.). Emulsifier Ex. 2 was shown to have a higher R600 @ 40° F. value, a lower 3/6 rpm @ 150° F. value, a higher HPHT fluid loss, and a higher gel strength value, which were considered less desirable than that profile of Ex. 1.

When the emulsifier as described in the first step of FIG. 2 is prepared according to the described procedure, its performance is excellent. As shown in the rheological properties shown in Table 3 (Ex. 1) a low shear rate viscosity (LSRV) of 12.6 (R6) to 13 (R3) is high. This was found to be significant, as it is difficult to achieve a good LSRV without making the 600@40° F. rheology properties exceed a dial reading of 200.

Furthermore, achieving a good LSRV for a high temperature drilling fluid is challenging because commonly used reaction product (e.g., RMs or RMs based on amines) generally do not perform well after the hot rolling process. Examples of such reaction products include dimer amine, THIXATROL RM-14, and RHEFLAT PLUS.

Maintaining a low R600@40° F. value while boosting 3/6 rpm (LSRV) at 150° F. is a continual focus for SBM development teams. Typically, this is achieved with rheology modifiers such as RHECON and hexyl CARBITOL. It is operationally simpler, however, to use an emulsifier that provides a good LSRV without over-reliance on excessive addition of rheology modifier. Also, the emulsifier shown in the first step of FIG. 2 has a low gel value, similar to or better than the examples of commercially-available emulsifiers. This can be seen, for instance, in the SBM formulation shown in Table 4, with the corresponding properties shown in Table 5.

TABLE 3

SBM Properties

| Emulsifier | Ex. 1 | | Ex. 2 | | Ex. 5 | | Ex. 6 | |
| --- | --- | --- | --- | --- | --- | --- | --- | --- |
| Rheology Temp (° F.) | 40 | 150 | 40 | 150 | 40 | 150 | 50 | 150 |
| R600 (° VG) | 186 | 91 | 233 | 73 | 220 | 88 | 189 | 49 |
| R300 (° VG) | 106 | 63 | 132 | 46 | 127 | 49 | 104 | 29 |
| R200 (° VG) | 76 | 51 | 94 | 34 | 88 | 40 | 73 | 21 |
| R100 (° VG) | 43 | 36 | 57 | 21 | 53 | 28 | 40 | 13 |
| R6 (° VG) | 8.8 | 12.6 | 14.5 | 6.5 | 14 | 12 | 7.6 | 4.7 |
| R3 (° VG) | 6.7 | 13 | 13.3 | 6.2 | 12 | 12 | 6.3 | 4.4 |
| PV (cP) | 80 | 28 | 101 | 27 | 93 | 39 | 85 | 20 |
| YP (lb/100 ft$^2$) | 26 | 35 | 31 | 19 | 34 | 10 | 19 | 9 |
| LSYP (lb/100 ft$^2$) | 5 | 13 | 12 | 6 | 10 | 12 | 5 | 4 |
| 10-sec Gel (lb/100 ft$^2$) | 8.4 | 6.8 | 13.3 | 7.2 | 16 | 11.7 | 9 | 7.6 |
| 10-min Gel (lb/100 ft$^2$) | 14.7 | 9 | 21.5 | 14.3 | 28 | 19.3 | 17 | 15.4 |
| HTHP FL at 325° F. (ml) | 3.6 | | 10.4 | | 8.2 | | 17.4 | |
| Water in HTHP FL at 325° F. Filtrate (ml) | 0 | | 0 | | 0 | | 0.5 | |

TABLE 4

SBM Formulation

| Component | Mass (g) |
|---|---|
| AMODRIL 1000 | 139 |
| HAMPOSYL O | 7 |
| RHECON | 4 |
| SUREWET | 1.5 |
| VG 69 | 0.5 |
| Lime | 5 |
| 25% CaCl$_2$ Brine | 77.3 |
| DURAMOD | 13 |
| ECOTROL HT | 0.75 |
| RADIACID 1980 at 50% actives in mineral oil | 2.13 |
| MICROBAR | 351 |

TABLE 5

SBM Properties

| Rheology Temp, ° F. | 40 | 150 |
|---|---|---|
| R600, ° VG | 218 | 76 |
| R300, ° VG | 122 | 45 |
| R200, ° VG | 86 | 33 |
| R100, ° VG | 49 | 20 |
| R6 , ° VG | 6.5 | 5.7 |
| R3, ° VG | 4.9 | 5.7 |
| PV, cP | 96 | 31 |
| YP, lb/100 ft$^2$ | 26 | 14 |
| LSYP, lb/100 ft$^2$ | 3 | 6 |
| 10-sec Gel, lb/100 ft$^2$ | 8.8 | 13 |
| 10-min Gel, lb/100 ft$^2$ | 42 | 25 |
| HTHP FL at 325° F., ml | | 5.4 |
| Water in HTHP FL (325° F.) Filtrate, ml | | 0 | good ratio of R600@40° F. to 3/6 rpm at 150° F. The HPHT result is also good, and gels are low for this 325° F. formulation. Reducing the SWR reduces the system cost to a much greater extent than changing or substituting other additives. For economic reasons a lower SWR can be significant.

TABLE 6

SBM Formulation

| Component | Mass (g) |
|---|---|
| AMORDRIL 1000 | 122 |
| EMULSIFIER | 12 |
| Hexyl CARBITOL | 4 |
| SUREWET | 1.5 |
| VG 69 | 0.5 |
| Lime | 5 |
| 25% CaCl$_2$ Brine | 102.2 |
| DURAMOD | 3 |
| ECOTROL HT | 0.75 |
| SUREMOD | 2.13 |
| MICROBAR | 347 |

TABLE 7

SBM Properties

| Emulsifier | Ex. 1 | | Ex. 7 | | Ex. 8 | |
|---|---|---|---|---|---|---|
| Rheology Temp (° F.) | 40 | 150 | 40 | 150 | 40 | 150 |
| R600 (° VG) | 157 | 66 | 414 | 95 | 221 | 71 |
| R300 (° VG) | 90 | 46 | 281 | 58 | 121 | 44 |
| R200 (° VG) | 65 | 36 | 225 | 43 | 85 | 33 |
| R100 (° VG) | 38 | 24 | 156 | 26 | 49 | 21 |
| R6 (° VG) | 7.3 | 6.6 | 43 | 5 | 10 | 11 |
| R3 (° VG) | 5.8 | 5.7 | 39 | 4 | 8.8 | 11 |
| PV (cP) | 67 | 20 | 133 | 37 | 100 | 27 |
| YP (lb/100 ft$^2$) | 23 | 26 | 148 | 21 | 21 | 17 |
| LSYP (lb/100 ft$^2$) | 4 | 5 | 35 | 3 | 8 | 11 |
| 10-sec Gel (lb/100 ft$^2$) | 6.1 | 5.9 | 32 | 4.7 | 11 | 10.5 |
| 10-min Gel (lb/100 ft$^2$) | 7.4 | 6.1 | 174 | 4.9 | 25 | 14 |
| HTHP FL at 325° F. (ml) | 2 | | 0.9 | | 36 | |
| Water in HTHP FL at 325° F. Filtrate (ml) | 0 | | 0 | | 3 | |

Specifically, Tables 4 and 5 show the formulation and properties of an SPM prepared based on commercially available HAMPOSYL O (N-Oleoyl sarcosine) emulsifiers. The prepared mud is a 14.19 ppg OBM with an oil-to-water ratio of 78:22, and was hot-rolled at 325° F. for 16 hours.

Based on the favorable rheological profile and HPHT result demonstrated for emulsifier Ex. 1, it was determined that type of emulsifier is suitable for producing drilling fluids at a lower SWR (synthetic oil-water ratio). Decreasing the SWR has a favorable implication for the cost of the drilling fluid. As an example, a formulation using emulsifier Ex. 1 is presented in Table 6, with the properties in Table 7. Notably, even at decreased SWR it is still possible to achieve Notably, there may be a difference between different anhydrides that can be used to synthesize this emulsifier (see Table 1), and some may be more effective than others. Table 3 compares succinic, maleic, glutaric, phthalic and anhydride capping agents. It follows from the data shown in Table 3 that selection of the capping agent can be significant when preparing the emulsifier for the purpose of achieving the lowest R600@40° F., lowest HPHT, and gel properties (or balancing such properties).

In this particular example, emulsifier Ex. 1 based on oleyl amine (201-1) and succinic anhydride (201-2) performs very well at 325° F. when synthesis is executed under highly controlled conditions and the amide product is preferentially produced. This emulsifier can also be used to formulate high temperature drilling fluids with a reduced synthetic-water ratio. It is further expected that the Ex. 1 emulsifier would perform exceptionally well at lower temperatures. Since a large number of wells drilled have bottom hole temperature less than 325° F., Ex. 1 should have applicability for many different jobs.

INDUSTRIAL APPLICABILITY

Emulsifiers of the simplest form can include various fatty acid soaps, such as tall oil, oxygenated tall oil, and resin acid, optionally in a calcium soap form. The soaps may be formed in-situ in the OBM via the addition of desired fatty acid and a base such as lime.

Figure 13:
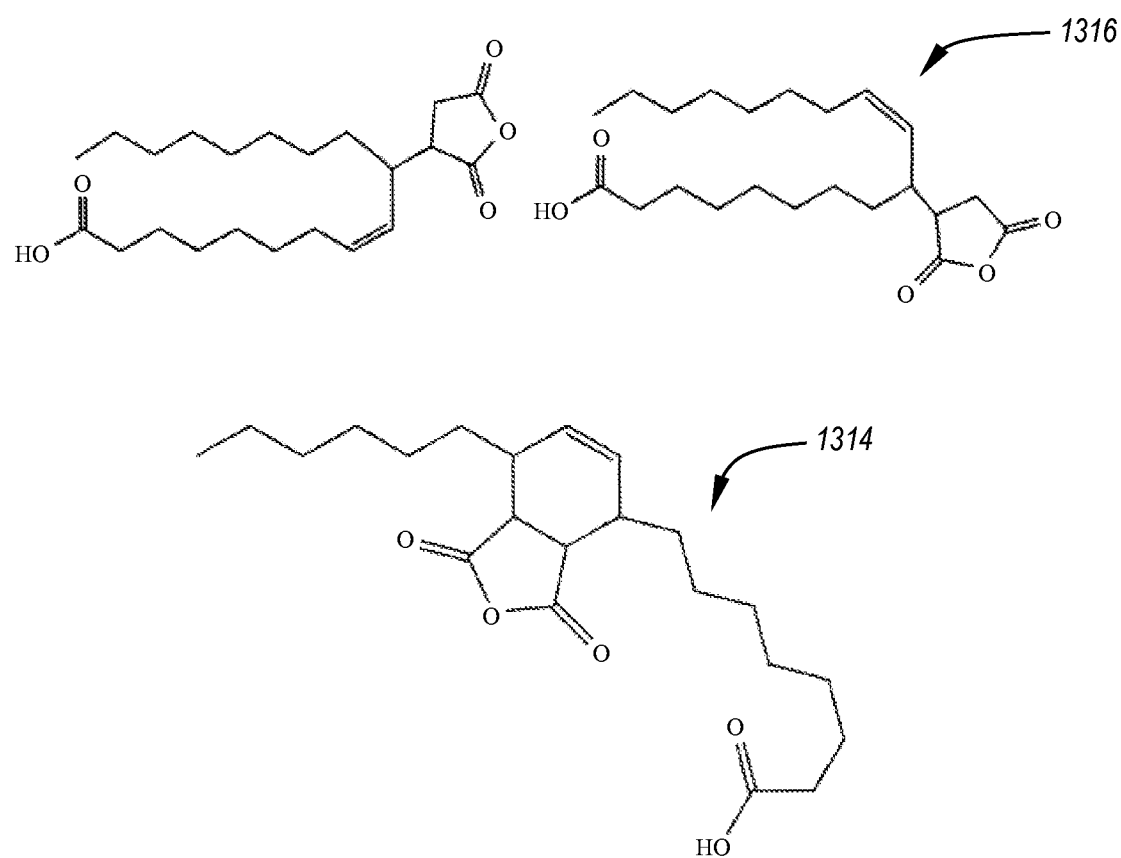
FIG. 13 shows formulas including Dies-Alder and ene reaction products, according to some embodiments of the present disclosure.

Other emulsifiers include compositions including derivatized compounds in which the compounds are both maleated and oxidized. The derivatized compounds can be derivatized dimer (or trimer) type acids based on fatty acids and rosin acids. Representative sets of structures of molecular species potentially found in maleated tall oil compositions suitable for use as the starting material for making chemically modified oxidized and maleated unsaturated fatty acid compositions include Dies-Alder reaction products (e.g., structure 1314) with conjugated linoleic acid and ene reaction products 1316 with oleic and elaidic acids such as those shown in FIG. 13.

Figure 14:
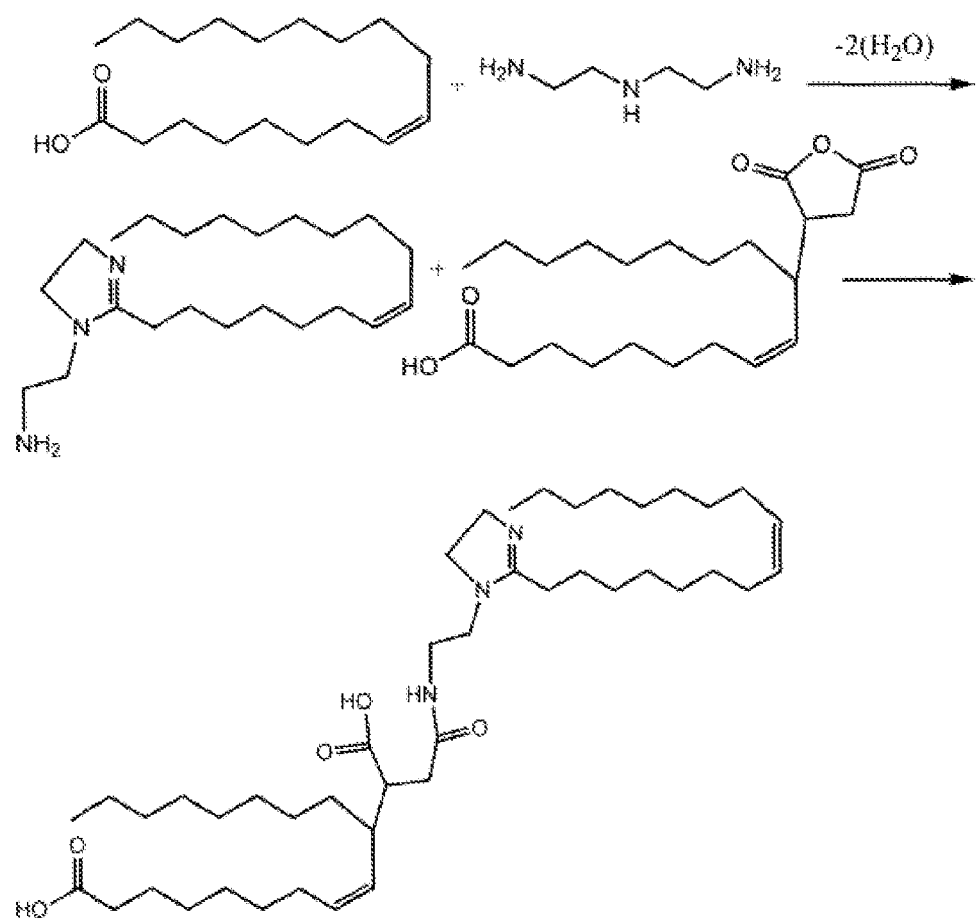
FIG. 14 shows formulas for derivatized oxmal compound (s), according to some embodiments of the present disclosure.

The carboxylic acid of an oxmal compound can be further chemically modified with a polyamine, an amino alcohol, an imidazoline, a metal chelator, an acetylenic alcohol, a morpholino moiety, a phosphate ester, an amino acid, a Xanthate, a thiophosphate ester, a hydroxamic acid, a sulfonate, a sulfate, or other molecules. In one example, fatty imidazoline derivatized oxmal compounds can be produced by preparing the fatty imidazoline, amidating the fatty imidazoline by reacting with a maleated unsaturated fatty acid compound, and then oxidizing the resulting compound to prepare the oxmal derivative compound, such as shown in the reaction in FIG. 14.

Figure 15:
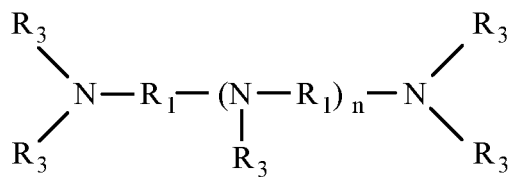
FIG. 15 is a formula of an amino compound, according to some embodiments of the present disclosure.

Well drilling fluids can also include an oil-in-water emulsion stabilized by a quaternary ammonium cellulosic derivative formed through the reaction of a carboxyalkyl cellulose compound with a quaternary ammonium compound. In an example of a water-in-oil emulsion, the emulsion can be stabilized by a polybasic fatty acid polymer resulting from the polymerization of an unsaturated fatty acid, a water-soluble alkaline earth metal salt and an amino compound corresponding to the group represented by the formula in FIG. 15. In such an example, the moieties represented by $R_1$ can each independently represent alkylene groups selected from those having 2 to 6 carbon atoms, n=0 to 5 and each $R_3$ can independently be selected from a class including hydrogen and —(RO)$_m$H groups, with RO being selected from ethylene oxide, propylene oxide, butylene oxide, and mixtures thereof, and m being an integer number of at least one but less than five.

Figure 16:
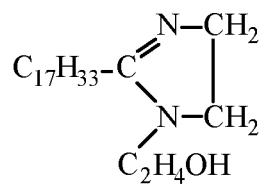
FIG. 16 shows formulas of an aliphatic imidazoline, and a diamine according to some embodiments of the present disclosure.
Figure 16:
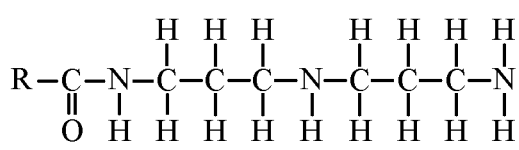

In further examples, aliphatic amido-diamines, aliphatic amido-polyamines, and aliphatic heterocyclic amines containing two nitrogen atoms in the ring structure, and preferably an aliphatic imidazoline, can be used as shown in FIG. 16.

Three-component emulsifying compositions including an amine-fatty acid condensate produced by reacting equimolar amounts of fatty acid and amine, a long chain aliphatic or fatty, monohydric alcohol, and a coupling agent such as an oil soluble solvent, can also be used.

In another example, a wetting agent/emulsifier composition can be formed through the reaction of synthetic linear saturated fatty acids and polyamines such as diethylenetriamine (DETA), triethylenetetramine (TETA), or tetraethylenepentamine (TEPA) under the particular conditions specified. Accordingly the product can be a polyamide imidazoline mixture prepared by reacting a synthetic linear saturated fatty acid with a polyamide in the presence of an acid, forming a polyamide condensate in the first set of reaction conditions (e.g., at 160° C.), eliminating water from the polyamide condensate, and forming the mixed polyamide imidazolines in a second set of reaction conditions (e.g., at 190° C.).

Another polymeric emulsifier composition can include the reaction product (a first polymer) of a dimer or trimer fatty acid and a di- or poly-alkylene polyamine (e.g. diethylene triamine, DETA). A second polymer can be prepared by reacting the first polymer and other dibasic acids at temperatures of 130 to 200° C., for example, with an appropriate monobasic acid such as stearic acid.

In another invert emulsion drilling fluid based on polyamido amines, a reaction can be represented by the equation:

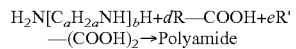
—(COOH)$_2$→Polyamide

These polyamide emulsifiers can be prepared by first reacting a polyamine (such as DETA) with a fatty acid (e.g., at 200 to 210° C.) for a period of time (e.g., 1 hour) to form an amidoamine. The amidoamine intermediate may then be reacted with a dicarboxylic acid such as maleic or fumaric acid, which contains from four to eight carbon atoms, and at a lower temperature (e.g., 160° C.). Longer reaction times may be necessary to ensure that the reaction goes to completion. Additionally, the emulsifier may be combined with a suspending agent such as an organophilic clay, which is produced as a reaction product of a clay and a quaternary ammonium salt.

Figure 17:
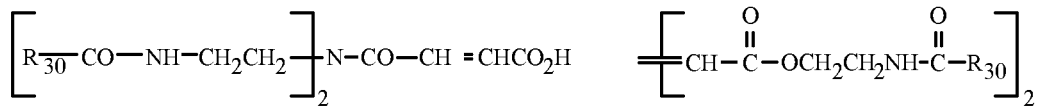
FIG. 17 is a formula of a maleic acid derivative, according to some embodiments of the present disclosure.

A further emulsifier composition can be formed as a reaction product of one or two moles of an amide-amine (having at least one free amino group) or a hydroxyalkyl amide having at least one hydroxy group, with one to five moles of a dicarboxylic acid or an acid anhydride (e.g., maleic anhydride, succinic anhydride, glutonic anhydride, diglycolic anhydride, or itaconic anhydride) and is depicted by the general formula (for maleic acid derivatives) as shown in FIG. 17. The $R_{30}$ component can be an oleyl derived from tall oil fatty acid.

Figure 18:
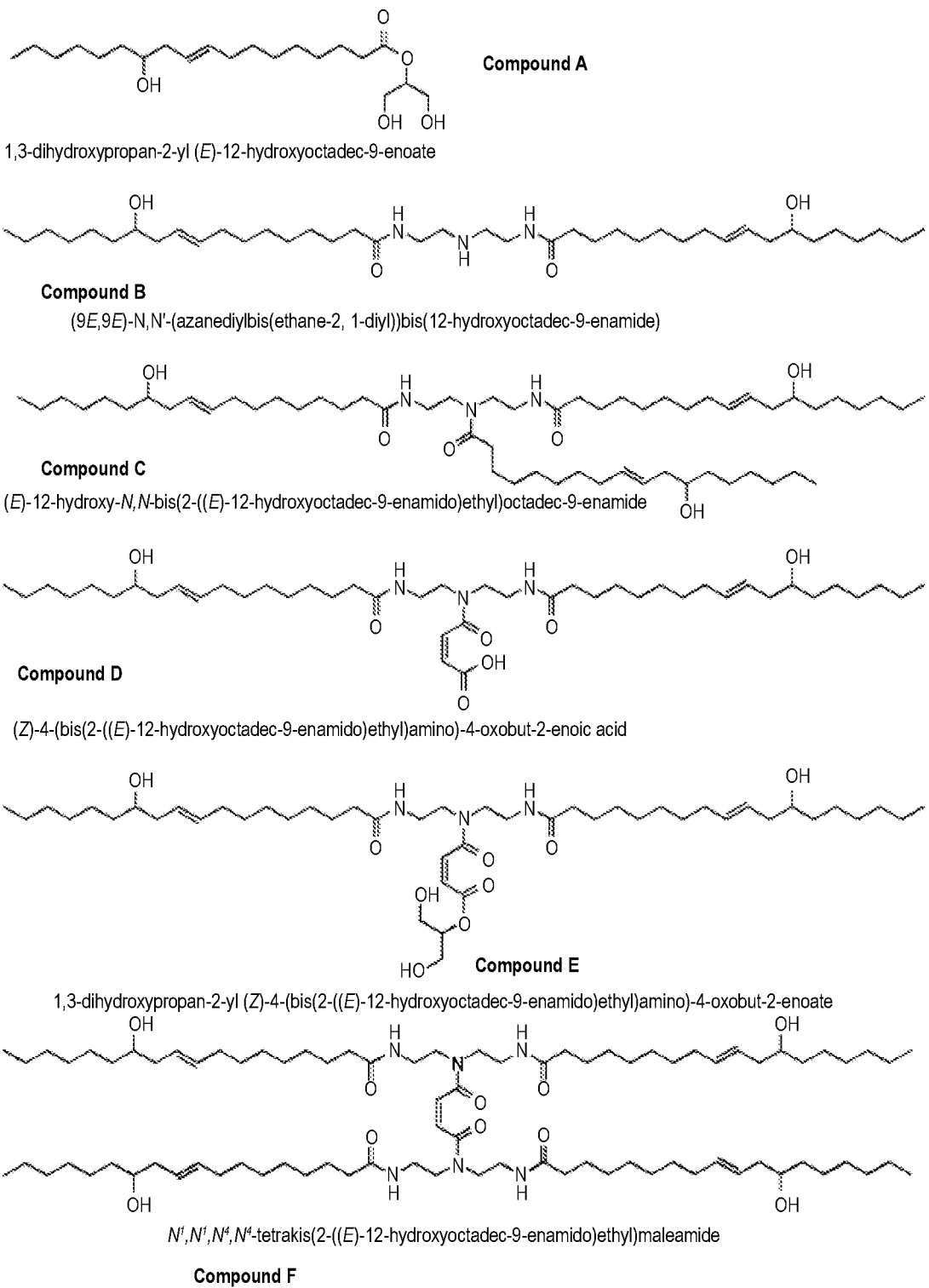
FIG. 18 shows formulas of emulsifier compounds, which are polyamides produced from reaction of a fatty oil with diethylenetriamine and maleic acid, according to some embodiments of the present disclosure.

Another emulsifier composition includes a mixture of polyamides produced from the reaction of a fatty oil (e.g., castor oil) with diethylenetriamine and then maleic acid. The composition can be include one or more compounds seen in FIG. 18 and can include 10-50 wt % oleyl alcohol, 10-50 wt % compound A, 5-30 wt % compound B, and 5-40 wt % of each of compounds C, D, E, and F.

Figure 19:
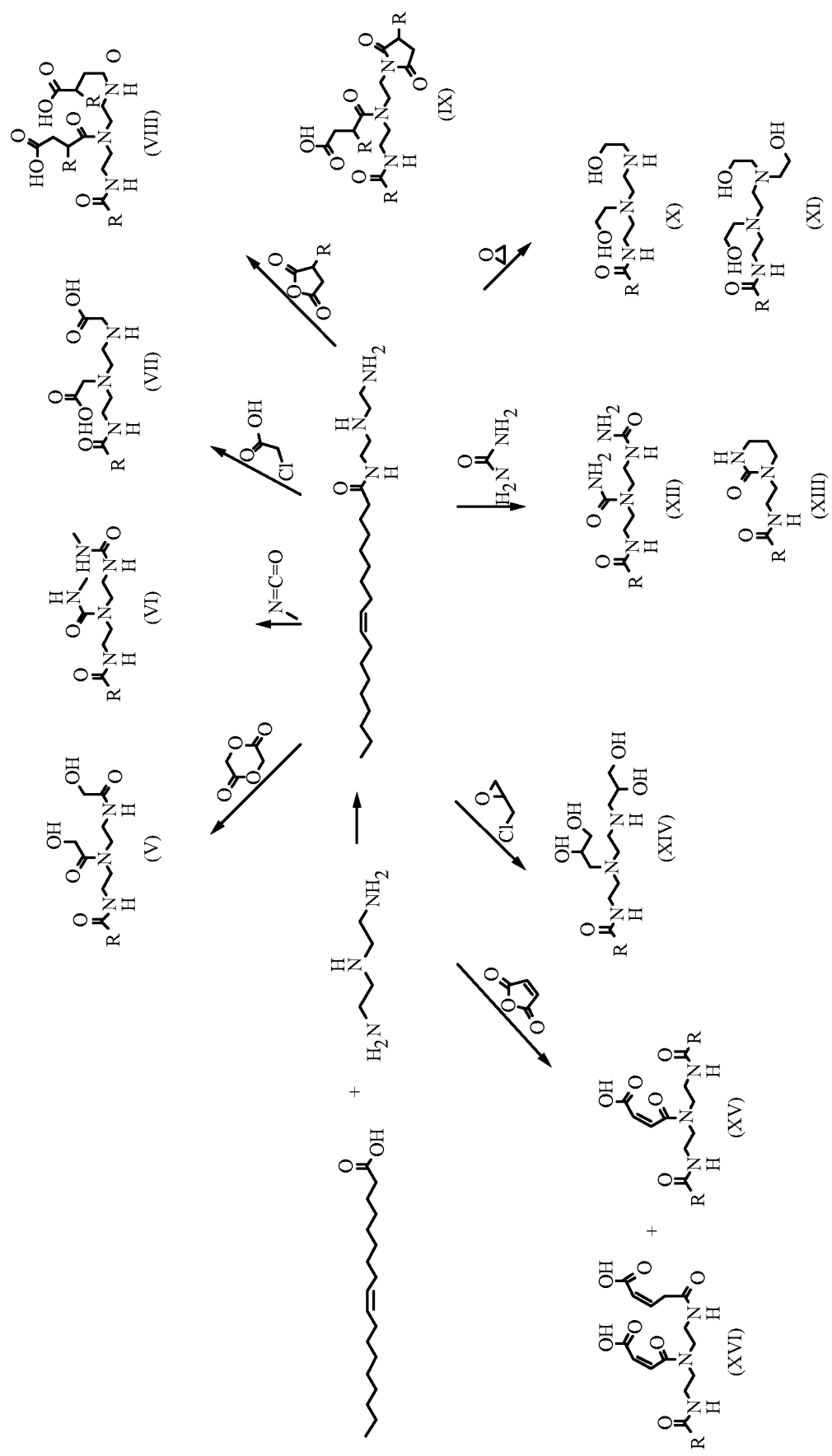
FIG. 19 shows formulas of emulsifier compounds produced from a reaction of a fatty acid and a hydrophilic compound, according to some embodiments of the present disclosure.
Figure 20:
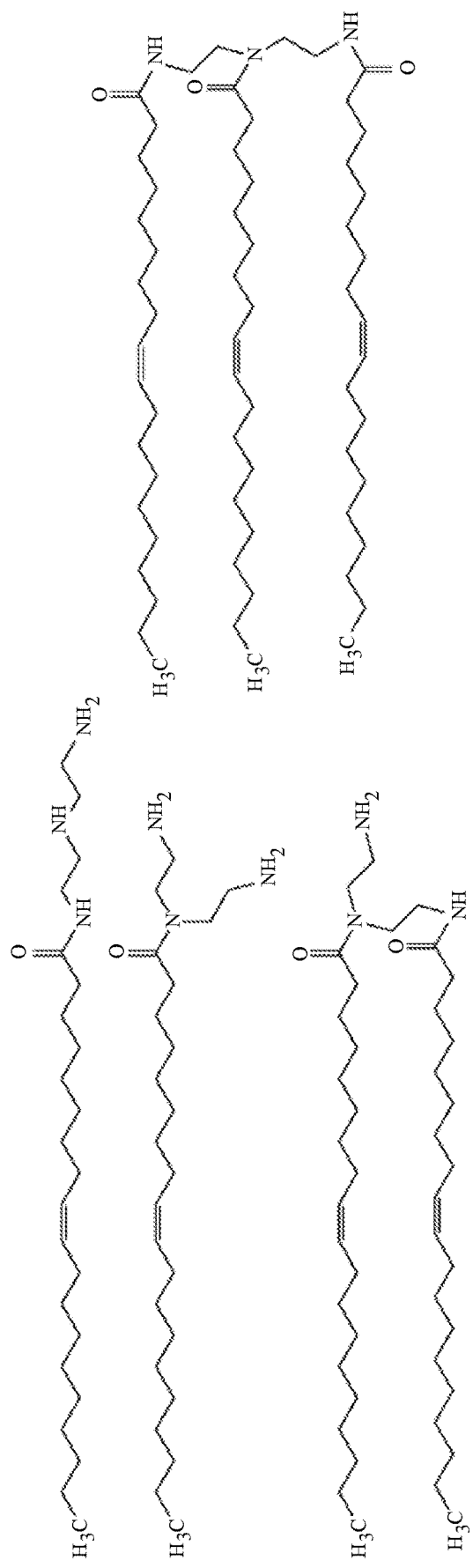
FIG. 20 shows formulas of compounds including reactive hydrophilic functional groups, according to some embodiments of the present disclosure.

A further emulsifier compound (see FIG. 19) can be produced from a capping agent reacted with a base emulsifier, wherein the base emulsifier is a reaction product of a fatty acid and a hydrophilic compound having at least two reactive hydrophilic functional groups as shown in FIGS. 19-20. FIG. 19 shows an example of reaction between oleic acid and diethylenetriamine. The capping agent can be one or more of a polycarboxylic acid, anhydride, urea, isocyanate, alpha-halocarboxylic acid, oxirane, cyclic diester, or cyclic sulfonate ester. Several examples of such are shown in FIG. 19.

In still another example, a polyamide emulsifier has the formula shown in FIG. 21, which can be prepared via a condensation reaction between polyamines (I) and fatty acids (II). The fatty acids and polyamines are reacted in such proportions as to create an amidoamine intermediate product (III). This intermediate (III) is then further reacted with maleic anhydride (IV) at a molar ratio of 0.75 to 1.25 to produce the polyamide emulsifier (V). Suitable fatty polyamines that are commercially available include DUOMEEN C (N-coco-1,3 diaminopropane), DUOMEEN S (N-soya-1,3, diaminopropane), DUOMEEN T (N-tallow, 1,3 diamino propane), and DUOMEEN O (N-oleyl, 1,3 diamino propane).

A further OBM composition can include a liquid tertiary amide $R_1$—CO—$NR_2R_3$ selected from the group of cyclic or acyclic liquid tertiary amides, while a further invert emulsifier may be based on the reaction of DETA with a fatty acid or fatty acid anhydride to produce a fatty amide which is subsequently reacted with a fatty acid. Reactions may be performed at a predetermined temperature, with the maleic anhydride or fumaric acid reaction taking place at 200 to 220° C., for example, over a time period such as 2 to 4 hours, while the DETA reaction can occur at temperatures such as 200 to 265° C. The subsequent fatty acid reaction can also occur at around 220° C.

An example branched amidoamine surfactant may also be prepared from the reaction between an alkylene amine or an oligoalkylene amine and a branched acid comprising a C4 to C24 primary hydrocarbon chain and having one or more C1 to C24 branches. Two embodiments of the emulsifier are shown in FIG. 22, with the example C4 branched acids being maleic and succinic acid.

Figure 23:
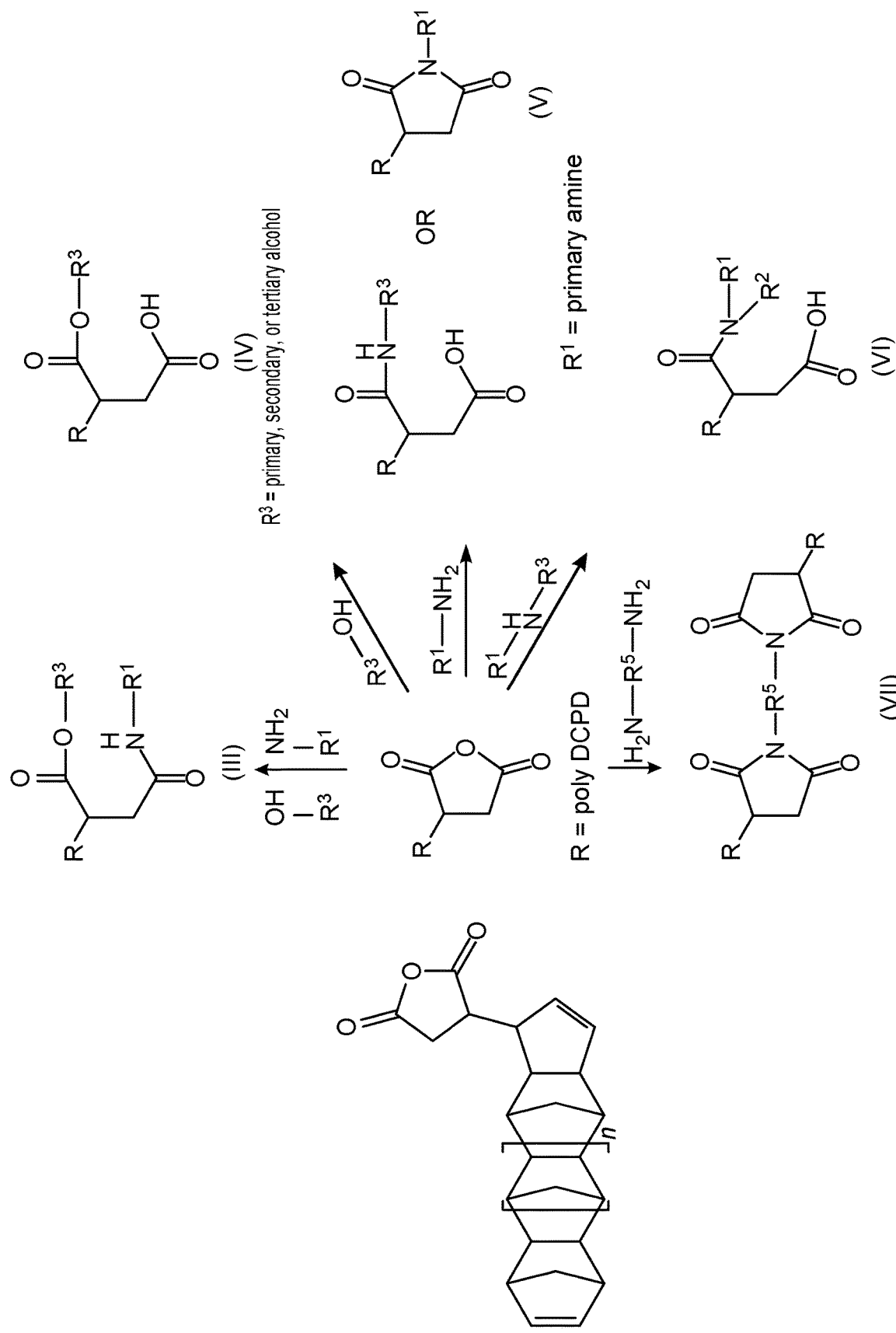
FIG. 23 shows formulas of polymeric emulsifiers with a polycyclic backbone formed by a copolymerization reaction at a terminal end of the polymer, according to some embodiments of the present disclosure.

Yet another invert emulsion wellbore fluid can contain a polymeric emulsifier with a polycyclic backbone and with at least one dicyclopentadiene repeating unit. The polycyclic backbone of the polymer may be formed via a copolymerization reaction of dicyclopentadiene (DCPD) and maleic anhydride at the terminal end of the polymer as shown in FIG. 23. As the anhydride group acts as the head group of the surfactant polymer, it can be reacted further with primary alcohols or primary amines or other amines, for example, to further tailor the specific properties of the invert emulsion fluid.

Figure 24:
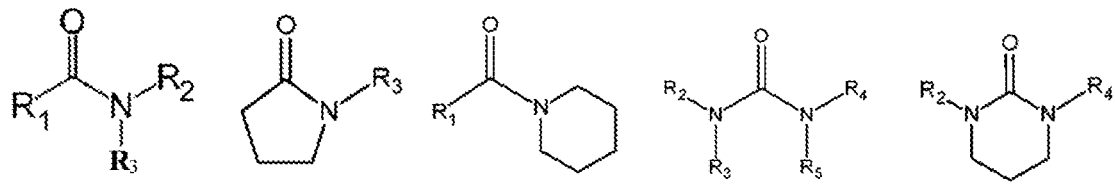
FIG. 24 is a set of formulas of cyclic and acyclic liquid tertiary amides, according to some embodiments of the present disclosure.

In another example, liquid tertiary amides can be used as pour point depressants, and selected from the group of cyclic or acyclic liquid tertiary amides shown in FIG. 24. In such an example, $R_1$, $R_2$, $R_3$, etc. are the same or different C5-C16 saturated and unsubstituted hydrocarbon chains.

In addition to emulsions, chemistry-related aspects of rheology additives may also be relevant to the present disclosure. A significant portion of 'flat rheology' additives (i.e. additives that can modulate the rheological properties of a drilling fluid in response to environmental temperature) can be produced from a reaction between oleophilic fatty acids and polyamines. These liquid additives can be used to tune the cold and high temperature rheological properties of drilling fluids, which can be important in drilling operations when performed in environments in which a wide temperature range is encountered (e.g. subsea drilling).

Examples of rheology additives are unsaturated fatty acids, as monomers but also in a dimer, trimer and fatty poly-carboxylic acid forms. These additives can be used to increase viscosity under low shear rate conditions. Several liquid rheology modifiers are commercially available from the M-I SWACO of Schlumberger Limited, and include SUREWET, SUREMOD, and REFLAT.

An example composition that may be used to provide flat temperature rheology can include the reaction product of a dimer fatty acid and a polyethylene polyamine such as DETA blended with alkoxylated alkyl amines and fatty acid amides.

In another example, a 'thinner' can be represented by the formula

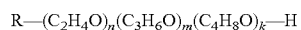

$$R—(C_2H_4O)_n(C_3H_6O)_m(C_4H_8O)_k—H$$

where n, m and k relate to the number of ethylene oxide, propylene oxide, and butylene oxide molecules (or groups per molecule) of the alkoxylated fatty alcohol.

Figure 25:
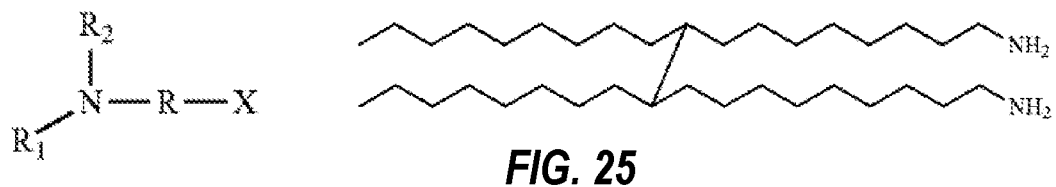
FIG. 25 is a molecular structure of a hydrophobic amine rheology modifier, according to some embodiments of the present disclosure.

Another stabilizing additive may have a hydrophobic amine rheology modifier including a C36 fatty dimer diamine represented by the molecular structure in FIG. 25. For the other structure illustrated in FIG. 25: R is a hydrophobic group with the number of carbon atoms ranging from 16 to 54; N is a primary, secondary, or tertiary amine; X is a hydrophilic group such as a primary, secondary, or tertiary amine, an amide, amine oxide, betaine or ester, etc.; and the $R_1$ and $R_2$ groups can independently be a hydrogen group, an alkyl group, cyano alkyl group, amino alkyl group, etc.

Figure 26:
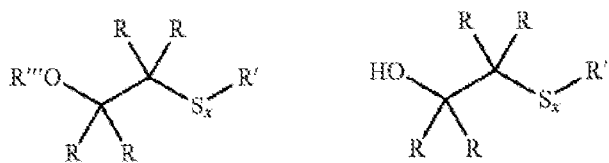
FIG. 26 is a formula of a rheology modifier, according to some embodiments of the present disclosure.

Another rheological additive can be derived from a condensation reaction of polycarboxylic acids, such as dimer acids with alkoxylated nitrogen containing compounds and polyetherdiamines which contain ≥2 active hydrogen groups. A further rheology modifier can be derived from the reaction product of a polysulfide, a dimer acid, and a polyfunctional amine as shown in FIG. 26, where each R, R', and R''' can be independently selected from a group consisting of hydrogen and an organyl group, where x>2.

Still further rheology modifiers can include an ethoxylated alcohol compound with the formula $R^1$—(OCH$_2$—CH$_2$)$_x$—OH, in which $R^1$ is a saturated or unsaturated, linear or branched hydrocarbyl group having between 8 to 20 carbon atoms. More generally, x can be an integer from 1 to 10, and the surfactant can have a hydrophilic-lipophilic balance (HLB) value of 8 to 16.

A drilling fluid composition may also include a blend of $R^1$—(OCH$_2$—CH$_2$)$_x$—OH and $R^2$—CO—NH—CH$_2$—CH$_2$—N(COR$^2$)—CH$_2$—CH$_2$—NH—COR$^3$, where $R^2$ is hydrocarbyl group with 1 to 20 carbon atoms and $R^3$ is a hydrocarbyl group with 1 to 10 carbon atoms, or an alkylene carboxylate group represented by —$R^4$—COOH, where $R^4$ is a saturated or unsaturated hydrocarbylene possessing 1 to 10 carbon atoms.

Figure 27:
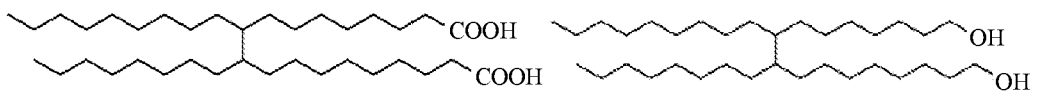
FIG. 27 shows formulas of a saturated dimer diacid and a fatty dimer diol, according to some embodiments of the present disclosure.

Another invert emulsion fluid may include a 36-carbon saturated dimer diacid and a 36 carbon fatty dimer diol as shown in FIG. 27. Another viscosifier package can include a fatty acid with 6 or more carbon atoms, as well as an aliphatic polyester.

Figure 28:
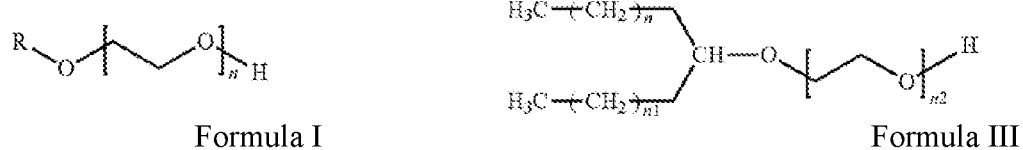
FIG. 28 shows formulas of rheology modifiers, according to additional embodiments of the present disclosure.

In still another example, a rheology modifier may be selected from alcohol ethoxylates, amine ethoxylates, or ethylene oxide/propylene oxide copolymers, where the rheology modifier has an HLB value ranging from 4 to 10. In FIG. 28, the R may be a C10-C26 alkyl group (either linear or branched, saturated, or unsaturated) and n=2-5 for the primary alcohol ethoxylate (Formula I) and n+n1=12 and n2=2-4 for secondary alcohol ethoxylate (Formula III).

The emulsifiers disclosed herein may be packaged within any appropriate emulsifier system, for use in invert-emulsion wellbore drilling fluids (OBM, SBM), or other wellbore drilling fluids. By way of general example, such an emulsifier system can include a diluent oil (e.g., a hydrocarbon with relatively high flash point) and a pour point depressant (e.g., an alkyl glycol with relatively high flash point). Those of skill in the art will appreciate the details of such selections. Examples of such are described in WO2018125651 and U.S. Pat. No. 11,066,591, each of which is herein incorporated by reference in its entirety.

Despite these various emulsions and additives described in this section, the applicant has identified a need to improve the performance of emulsifiers used in invert-emulsion drilling fluids (OBM, SBM). Despite significant development efforts, the most predominantly-used class of oil-based drilling fluid emulsifiers are amidoamines formed from the reaction between tall oil fatty acid (TOFA), diethylenetriamine (DETA), and maleic/succinic anhydrides. For many applications, these amidoamines are perceived as adequate, and other newly developed emulsifiers do not provide sufficient improvement to warrant their replacement. Additionally, when developing emulsifiers for high temperature applications, chemistry options can be limited by the stability to degradative processes (oxidative, hydrolytic stability, etc.). Emulsifiers based on amide chemistry perform satisfactorily in this regard; however, such amidoamines can have limitations. Synthesis of standard amidoamines may include a two-step high-temperature process that includes reacting DETA with TOFA, followed by reacting the reaction products with maleic anhydride. This process can be time consuming and complex from a manufacturing perspective. A second issue is that following synthesis, current emulsifiers have physical properties which are not optimal for efficient formulation.

Any "R" or "$R_x$" substituents which are otherwise not defined herein, may be as defined for any other "R" or "$R_x$" substituent, or may be hydrogen or any of various organic groups, such as linear or branched, saturated, unsaturated or substituted hydrocarbon chains (e.g., having 1 to 50, 1 to 30, 1 to 24, or 1 to 16 carbon atoms).

Any "m" "y" "n" or similar notations which are otherwise not defined herein, may be as defined for any other similar notations, or may be any of various integer values, such as 0, 1, 2, 3, etc.

As used herein, the term "between" includes any referenced endpoints. For example, "between 60 and 80" includes both 60 and 80.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% from the stated amount, value, or condition.

All publications, patents and patent applications cited herein, whether supra or infra, are hereby incorporated by reference in their entirety to the same extent as if each individual publication, patent or patent application was specifically and individually indicated to be incorporated by reference.

It will be appreciated that the embodiments and examples described in detail above can be modified and varied within the scope of the concepts which they exemplify. Proportions may be varied and may not be as shown in the drawings which are schematic and intended to explain layout and function of the embodiments. Features referred to above or shown in individual embodiments above may be used together in any combination as well as those which have been shown and described specifically. More particularly, where features were mentioned above in combinations, details of a feature used in one combination may be used in another combination where the same feature is mentioned. Accordingly, all such modifications are intended to be included within the scope of this disclosure as defined in the following claims.

What is claimed is:

1. A wellbore fluid, comprising:
an oleaginous external phase;
a non-oleaginous internal phase; and
an emulsifier composition that includes a reaction product of i) a primary fatty amine component and ii) a capping agent selected from the group consisting of a cyclic anhydride or a diacid, wherein the reaction product comprises at least one of a first structure and a second structure, wherein the first structure includes a) a non-terminal amide group derived from an amine group of the primary fatty amine component and a carboxyl group of the capping agent and b) a terminal carboxylic acid group derived from the capping agent, and wherein the second structure includes a terminal cyclic group derived from ring closing of the non-terminal amide group and the terminal carboxylic acid group of the first structure.

2. The wellbore fluid of claim 1, wherein the primary fatty amine component has an alkyl chain length of about 12 to 70 carbons.

3. The wellbore fluid of claim 1, wherein the primary fatty amine component is selected from the group consisting of oleyl amine, linoleyl amine, tall oil amine, or tallow amine.

4. The wellbore fluid of claim 1, wherein the capping agent is cyclic anhydride.

5. The wellbore fluid of claim 4, wherein the cyclic anhydride includes one or more of maleic anhydride, succinic anhydride, alkenyl succinic anhydride, alkyl succinic anhydride, glutaric anhydride or phthalic anhydride.

6. The wellbore fluid of claim 1, wherein the reaction product includes the Structure A formed at a temperature of about 60 to about 80° C.

7. The wellbore fluid of claim 1, wherein the reaction product includes the first structure formed at a temperature of about 60 to about 80° C., and further includes the second structure formed at a temperature of about 100 to about 180° C.

8. The wellbore fluid of claim 1, further comprising one or more rheology additives.

9. The wellbore fluid of claim 8, wherein the one or more rheology additives include one or more of fatty acids, dimers, trimers, Rhecon, or hexyl carbitol series additives.

10. The wellbore fluid of claim 1, wherein the primary fatty amine component has an amine group having nitrogen bonded to a single carbon.

11. The wellbore fluid of claim 1, wherein the reaction product includes the first structure, wherein the non-terminal amide group is positioned between the terminal carboxylic acid group and a carbon chain in the first structure.

12. A wellbore fluid emulsifier, comprising:
a reaction product of i) a primary fatty amine component and ii) a capping agent selected from the group consisting of a cyclic anhydride or a diacid;
wherein the reaction product comprises at least one of a first structure and a second structure, wherein the first structure includes a) a non-terminal amide group derived from an amine group of the primary fatty amine component and a carboxyl group of the capping agent and b) a terminal carboxylic acid group derived from the capping agent, and wherein the second structure includes a terminal cyclic group derived from ring closing of the non-terminal amide group and the terminal carboxylic acid group of the first structure.

13. The emulsifier of claim 12, wherein the reaction product comprises a blend of the first structure and the second structure.

14. The emulsifier of claim 13, wherein the capping agent is succinic anhydride and the reaction product includes a molecule of the following structure:

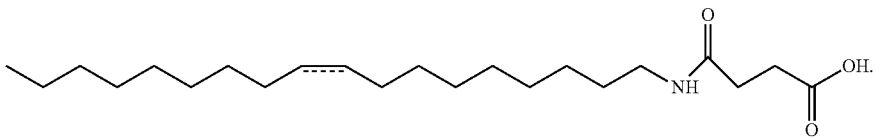

15. The emulsifier of claim 14, wherein the reaction product further includes a molecule of the following structure:

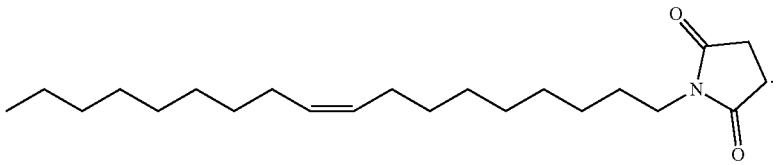 [SMILES: CCCCCCCC/C=C\CCCCCCCCN1C(=O)CCC1=O]

16. The emulsifier of claim 12, wherein the primary fatty amine component is selected from the group consisting of oleyl amine, linoleyl amine, tall oil amine, or tallow amine.

17. The emulsifier of claim 12, wherein the capping agent is cyclic anhydride.

18. The emulsifier of claim 12, wherein the primary fatty amine component has an amine group having nitrogen bonded to a single carbon.

19. The emulsifier of claim 12, wherein the reaction product includes the first structure, wherein the non-terminal amide group is positioned between the terminal carboxylic acid group and a carbon chain in the first structure.

* * * * *